United States Patent [19]

Wright et al.

[11] Patent Number: 5,952,189
[45] Date of Patent: Sep. 14, 1999

[54] ASSAY FOR INHIBITORS OF A 24 KD CYTOPLASMIC PROTEASE WHICH ACTIVATES DNA FRAGMENTATION IN APOPTOSIS

[75] Inventors: Susan C. Wright, Saratoga; James W. Larrick, Woodside, both of Calif.

[73] Assignee: Panorama Research, Inc., Mountain View, Calif.

[21] Appl. No.: 08/825,193

[22] Filed: Mar. 26, 1997

Related U.S. Application Data

[60] Continuation-in-part of application No. 08/741,631, Nov. 1, 1996, which is a division of application No. 08/259,752, Jun. 10, 1994, Pat. No. 5,605,826.

[51] Int. Cl.⁶ .............................. C12Q 1/37; C12N 9/64
[52] U.S. Cl. ............................................. 435/23; 435/226
[58] Field of Search ................................. 435/23, 24, 226

[56] References Cited

U.S. PATENT DOCUMENTS

| 5,298,407 | 3/1994 | Anderson et al. | 435/69.1 |
|---|---|---|---|
| 5,340,935 | 8/1994 | Anderson et al. | 536/23.5 |
| 5,360,893 | 11/1994 | Owens et al. | 530/350 |
| 5,605,826 | 2/1997 | Wright et al. | 435/226 |

FOREIGN PATENT DOCUMENTS

93/11246  6/1993  WIPO .

OTHER PUBLICATIONS

Balint R.F. et al., "Protease–Dependent Streptomycin Sensitivity in *E. coli*.—System for Protease Inhibitor Selection, " *Biotechnology* 13:507–510 (1995).
Billings, P.C. et al., "Potential Intracellular Target Proteins of the Anticarcinogenic Bowman Birk Protease Inhibitor Idfentified by Affinity Chromatography," *Cancer Res.* 48:1798–1802 (1988).
Block, T.M. et al., "Novel Bacteriological Assay for Detection of Potential Antiviral Agents," *Antimicro. Agents & Chemotherapy* 34 (13) :2337–2341 (1990).
Chandrasekaran, S. et al., "Purification of Subtilisin by Single–Step Affinity Chromatography," *Analyt. Biochem.* 150 (1) :141–144 (1985).
Cummings, A.D. et al., "Hemodynamic, renal, and hormonal actions of aprotinin in an ovine model of septic shock," *Critical Care Medicine* 20 (8) :1134–1139 (1992).
Darmon, A.J. et al., "The Cytotoxic T Cell Proteinase Granzyme B Does Not Activate Interleukin–1β–converting Enzyme," *J. Biol. Chem.* 269(51) : 32043–32046 (1994).
Dennis, M.S. et al., "Potent and Selective Kunitz Domain Inhibitors of Plamsa kallikrein Designed by Phage Display," *J. Biol. Chem.* 270 (43) :25411–25417 (1995).
Duvall, E. et al., "Death and the Cell," *Immunology Today* 7 (4) :115–119 (1986).
Ecker, D.J. et al., "Combinatorial Drug Discovery: Which Methods Will Produce the Greatest Value?" *Biotechnology* 13:351–360 (1995).
Eichler, J. et al., "Identification of Substrate–Analog Trypsin Inhibitors through the Screening of Synthetic Peptide Combinatorial Libraries," *Biochemistry* 32:11035–11041 (1993).
Erb, E. et al., "Recursive deconvolution of combinatorial chemical libraries," *Proc. Natl. Acad. Sci. U.S.A.* 91:11422–11426 (1994).
Gershenson, L.E. et al., "Apoptosis: A Different Type of Cell Death," *FASEB J.* 6:2450–2455 (1992).
Gold, R. et al., "Differentiation between Cellular Apoptosis and Necrosis by the Combined Use of In Situ Tailing and Nick Translation Techniques," *Lab. Invest.* 71(2) :219–225 (1994).
Green, D.R. et al., "Apoptosis and Cancer," *PPO Updates* 8(1):1–14.
Heusel, J.W., "Cytotoxic Lymphocytes Require Granzyme B for the Rapid Induction of DNA Fragmentation and Apoptosis in Allogeneic Target Cells," *Cell* 76(6):977–987 (1994).
Janda, K.D., "Tagged versus untagged libraries: Methods for the generation and screening of conbinatorial chemical libraries," *Proc. Natl. Acad. Sci. U.S.A.* 91:10779–10785 (1994).
Kwo, P. et al., "Nuclear serine protease actiity contributes to bile acid–induced apoptosis in hepatocytes," *Am. J. Physiol.* 268 (4 pt. 1) :G613–G621 (1995).
Larrick, J.W. et al., "Cytotoxic mechanism of tumor necrosis factor–α," *FASEB J.* 4:3215–3223 (1990).
Leist, M. et al., "Murine Hepatocyte Apoptosis Induced In Vitro and In Vivo by TNF–α Requires Transcriptional Arrest," *J. Immunol.* 153:1778–1788 (1994).
Leist, M. et al., "Activation of the 55 kDa TNF Receptor is Necessary and Sufficient for TNF–Induced Liver Failure, Hepatocyte Apoptosis, and Nitrite Release, " *J. Immunol.* 154:1307–1316 (1995).
Miura, M. et al., "Induction of Apoptosis in Fibroblasts by IL–1γ–Converting Enzyme, a Mammalian Homolog of the C. elegans Cell Death Gene ced–3," *Cell* 75:653–660 (1993).
Mossmann, T., "Rapid Colorimetic Assay for Cellular Growth and Survival: Application to Proliferation and Cytotoxicity Assays," *J. Immunol. Meth.* 65:55–63 (1983).
Nagaki, M. et al., "Hepatic Injury and Lethal Shock in Galactosamine–Sensitized Mice induced by the Superantigen Staphylococcal Enterotoxin B," *Gastroenterology* 106:450–458 (1994).
Ogasawara, J. et al., "Lethal effect of the anti–Fas antibody in mice," *Nature* 364:806–809 (1993).

(List continued on next page.)

*Primary Examiner*—Jon P. Weber
*Attorney, Agent, or Firm*—Townsend and Townsend and Crew LLP

[57] ABSTRACT

A method is disclosed for assaying for inhibitors of a 24 kDa cytoplasmic protease associated with apoptosis. The protease has a defined amino acid composition, activity against the elastase-like substrate MAAVP, and induces DNA fragmentation associated with apoptosis in isolated U937 cell target nuclei.

2 Claims, 9 Drawing Sheets

OTHER PUBLICATIONS

Ostrech, J.M. et al., "'Libraries from libraries': Chemical transformation of combinatorial libraries to extend the range and repertoire of chemical diversity," *Proc. Natl. Acad. Sci. U.S.A.* 91:11138–11142 (1994).

Owens, R.A. et al., "Rapid Identification of HIV Protease Inhbitors Through the Synthesis and Screening of Defined Peptide Mixtures," *Biochem. Biophys. Res. Comm.* 181 (1) :402–408 (1991).

Roberts, B.L. et al., "Protease inhibitor display M13 phage: selectionof high–affinity neutrophil elastate inhibitors," *Gene* 121:9–15 (1992).

Sarin, A. et al., "Protease Inhibitors Selectively Block T Cell Receptor–Triggered Programmed Cell Death in a Murine T Cell Hybridoma and Activated Peripheral T Cells," *J. Exp. Med.* 178 (15) :1693–1700 (1993).

Sasaki, Y. et al., "Solid Phas Synthesis of Peptides Containing the $CH_2NH$ Peptide Bond Isostere," *Peptides* 8:119–121 (1987).

Schlegel, J. et al., "Isolation and partial characterization of a protease involved in Fas–induced apoptosis," *FEBS Letts* 364:139–142 (1995).

Schwartzman, R.A. et al., "Inernucleosomal Deoxribonucleic Acid Cleavage Activity in Apoptotic Tymocytes: Detection and Endocrine Regulation," *Endocrinology* 128 (2) :1190–1197 (1991).

Shi, L. et al., "Purification of Three Cytotoxic Lymphocyte Granule Serine Proteases That Induce Apoptosis through Distinct Substrate and Target Cell Interations," *J. Exp. Med.* 176:1521–1529 (1992).

Siebeck, M. et al., "Leukocyte Neutral Proteinase Inhibitor of the Pig: Modification by Eglin C and Superoxide Dismutase," *Prog Clin. Biol. Res.* 308:945–951 (1989).

Sofer, G. et al., "Designing an Optimal Chromatographic Purification Scheme for Proteins," *Biotechniques* 1:198–203 (1983).

Squier, M. et al., "Calpain Activaion in Apoptosis," *J. Cell. Physiol.* 159 (2) :229–237 (1994).

Stewart, B.W., "Mechanisms of Apoptosis: Integration of Genetic, Biochemical, and Cellular Indicators," *J. Natl. Canc. Inst.* 86 (17) :1286–1296 (1994).

Wang, C.I. et al., "Isolation of a High Affinity Inhibitor of Urokinase–type Plasminogen Activator by Phage Display of Ecotin," *J. Biol. Chem.* 270 (20) :12250–12256 (1995).

Wang, E., "Senescent Human Fibroblasts Resist Programmed Cell Death, and Failure to Suppress bc12 Is Involved," *Canc. Res.* 55:2284–2292 (1995).

Weaver, V.M. et al., "Role of proteolysis in apoptosis: involvement of serine proteases in internucleosomal DNA fragmentation in immature thymocytes," *Biochm. & Cell Biol.* 71 (9–10) :488–500 (1993).

Wong, G.H.W. et al., "Fas Antigen and p55 TNF Receptor Signal Apoptosis Through Distinct Pathways," *J. Immunol.* 152:1751–1755 (1994).

Wright et al., "Apoptosis and DNA Fragmentation Precede TNF–Induced cytolysis in U937 Cells," *J. Cell. Biochem.* 48:344–355 (1992).

Wright et al., "Role of Protein Phosphorylation in TNF–Induced Apoptosis: Phosphatase Inhibitors Synergize with TNF to Activate DNA Fragmentation in Normal as Well as TNF–Resistant U937 Variants," *J. Cell. Biochem.* 53:222–233 (1993).

Wright, S.C. et al., "Nicotine inhibition of apoptosis suggests a role in tumor promotion," *FASEB J.* 7 (8) : 1045–1051 (1993).

Wright, S.C. et al., "Inhibition of apoptosis as a mechanism of tumor promotion," *FASEB J.* 8 (9) :654–660 (1994).

Wright, S.C. et al., "Purification of a 24–kD Protease from Apoptotic Tumor Cells That Activates DNA Fragmentation," *J. Exp. Med.* 180:2113–2123 (1994).

Yuan, J. et al., "The C. elegans Cell Death Gene ced–3 Encodes a Protein Similar to Mamalian Interleukin–1γ–Converting Enzyme," *Cell* 75:641–652 (1993).

Zhivotovsky, B. et al., "Formation of 50 kbp chromatin fragments in isolated lier nuclei is mediated by protease and endonuclease activation," *FEBS Letts* 351:150–154 (1994).

SEQUENCE LISTING

```
(1) GENERAL INFORMATION:

(iii) NUMBER OF SEQUENCES: 5

(2) INFORMATION FOR SEQ ID NO:1:

(i) SEQUENCE CHARACTERISTICS:
         (A) LENGTH: 4 amino acids
         (B) TYPE: amino acid
         (C) STRANDEDNESS:
         (D) TOPOLOGY: linear (ii) MOLECULE TYPE: peptide (xi) SEQUENCE DESCRIPTION: SEQ ID NO:1:

Ala Ala Pro Val
1

(2) INFORMATION FOR SEQ ID NO:2:

(i) SEQUENCE CHARACTERISTICS:
         (A) LENGTH: 4 amino acids
         (B) TYPE: amino acid
         (C) STRANDEDNESS:
         (D) TOPOLOGY: linear (ii) MOLECULE TYPE: peptide (ix) FEATURE:
         (A) NAME/KEY: Modified-site
         (B) LOCATION: 1
         (D) OTHER INFORMATION: /product= "OTHER"
             /note= "Xaa = N-succinyl-alanine"

(ix) FEATURE:
         (A) NAME/KEY: Modified-site
         (B) LOCATION: 4
         (D) OTHER INFORMATION: /product= "OTHER"
             /note= "Xaa = phenylalanine
             para-nitroanilide"
```

```
        (xi) SEQUENCE DESCRIPTION: SEQ ID NO:2:

Xaa Ala Pro Xaa
1

(2) INFORMATION FOR SEQ ID NO:3:

(i) SEQUENCE CHARACTERISTICS:
          (A) LENGTH: 4 amino acids
          (B) TYPE: amino acid
          (C) STRANDEDNESS:
          (D) TOPOLOGY: linear (ii) MOLECULE TYPE: peptide (ix) FEATURE:
          (A) NAME/KEY: Modified-site
          (B) LOCATION: 1
          (D) OTHER INFORMATION: /product= "OTHER"
              /note= "Xaa = N-methoxysuccinyl-alanine"

(ix) FEATURE:
          (A) NAME/KEY: Modified-site
          (B) LOCATION: 4
          (D) OTHER INFORMATION: /product= "OTHER"
              /note= "Xaa = valine
              para-nitroanilide"

(xi) SEQUENCE DESCRIPTION: SEQ ID NO:3:

Xaa Ala Pro Xaa
1

(2) INFORMATION FOR SEQ ID NO:4:

(i) SEQUENCE CHARACTERISTICS:
          (A) LENGTH: 4 amino acids
          (B) TYPE: amino acid
          (C) STRANDEDNESS:
          (D) TOPOLOGY: linear (ii) MOLECULE TYPE: peptide (ix) FEATURE:
          (A) NAME/KEY: Modified-site
          (B) LOCATION: 1
          (D) OTHER INFORMATION: /product= "OTHER"
              /note= "Xaa = N-methoxysuccinyl-alanine"

(ix) FEATURE:
          (A) NAME/KEY: Modified-site
          (B) LOCATION: 4
          (D) OTHER INFORMATION: /product= "OTHER"
              /note= "Xaa = valine thiobenzyl ester"

(xi) SEQUENCE DESCRIPTION: SEQ ID NO:4:

Xaa Ala Pro Xaa
1

(2) INFORMATION FOR SEQ ID NO:5:

(i) SEQUENCE CHARACTERISTICS:
          (A) LENGTH: 5 amino acids
          (B) TYPE: amino acid
          (C) STRANDEDNESS:
          (D) TOPOLOGY: linear (ii) MOLECULE TYPE: peptide (ix) FEATURE:
          (A) NAME/KEY: Modified-site
          (B) LOCATION: 1
          (D) OTHER INFORMATION: /product= "OTHER"
              /note= "Xaa = N-acetylated normal
              L-amino acids, excluding Arg, His, Trp,
              Lys or Cys"
```

```
    (ix) FEATURE:
         (A) NAME/KEY: Modified-site
         (B) LOCATION: 2
         (D) OTHER INFORMATION: /product= "OTHER"
              /note= "Xaa = normal L-amino acids,
              excluding Arg, His, Trp, Lys or Cys"

(ix) FEATURE:
         (A) NAME/KEY: Modified-site
         (B) LOCATION: 3
         (D) OTHER INFORMATION: /product= "OTHER"
              /note= "Xaa = Phe, Val, Leu, Ile,
              Ala or Tyr"

(ix) FEATURE:
         (A) NAME/KEY: Modified-site
         (B) LOCATION: 4
         (D) OTHER INFORMATION: /product= "OTHER"
              /note= "Xaa = normal L-amino acids,
              excluding Arg, His, Trp, Lys or Cys"

(ix) FEATURE:
         (A) NAME/KEY: Modified-site
         (B) LOCATION: 5
         (D) OTHER INFORMATION: /product= "OTHER"
              /note= "Xaa = normal L-amino acids,
              excluding Arg, His, Trp, Lys or Cys"

(xi) SEQUENCE DESCRIPTION: SEQ ID NO:5:

Xaa Xaa Xaa Xaa Xaa
1               5
```

ASSAY FOR INHIBITORS OF A 24 KD CYTOPLASMIC PROTEASE WHICH ACTIVATES DNA FRAGMENTATION IN APOPTOSIS

CROSS-REFERENCE TO RELATED APPLICATIONS

This application is a continuation-in-part of U.S. Ser. No. 08/741,631, filed Nov. 1, 1996, which is a divisional under 37 CFR 1.60 of U.S. Ser. No. 08/259,752 filed Jun. 10, 1994 (now U.S. Pat. No. 5,605,826) which are hereby incorporated by reference in their entirety for all purposes.

BACKGROUND OF THE INVENTION

Necrosis and apoptosis are two distinct modes of death for nucleated eukaryotic cells. Necrosis may occur as a result of cellular injury, typically complement attack, lytic viral infection, toxins and the like. Apoptosis or "programmed cell death", on the other hand, is the physiological process of cell death that functions to control cell populations during embryogenesis, immune responses, hormone withdrawal from dependent tissues, normal tissue homeostasis, and regressing tumors, as described in Duvall, E., et al. (1986) Immunol. Today 7, 115–119; Walker, N. I., et al. (1988) Meth. Achiev. Exp. Pathol. 13, 18–54; and Gerschenson, L. E. et al. (1992) FASEB J. 6;, 2450–2455. Unlike cellular necrosis, apoptotic cytolysis is not usually associated with cellular injury. Apoptosis may be induced by immunologically mediated methods, such as antibody dependent cell cytotoxicity (K cell attack), viral infection, and attack by cytotoxic T lymphocyte effector cells, lymphotoxins, or natural killer (NK) cells. Further, apoptosis may be induced in tumor cells by a variety of physical, chemical, and biochemical apoptosis inducing agents, including gamma radiation, UV light, heat shock, cold shock, cisplatin, etoposide, teniposides, DNA alkylating agents, macromolecular synthesis inhibitors, and the like.

Cytological and biochemical changes are associated with the cellular apoptotic process. The cytoplasm condenses, and the endoplasmic reticulum dilates to form vesicles which fuse with the cell membrane, producing characteristic cellular morphology. Changes in the nuclei include the formation of dense crescent shaped aggregates of chromatin, nucleolus fragmentation, and formation of vesicles at or on the nuclear membrane. During apoptosis endonucleases present in the cell cut the DNA in the linker regions between nucleosomes to release DNA fragments in integer multiples of 180–190 base pairs, Cohen J. J., et al. (1984) J. Immunol. 132, 38–42. The pattern of cleavage is believed to result from the vulnerability of the linker DNA between the nucleosomes to endonucleases.

However, the identification of the relevant nucleases involved in apoptosis has not yet been achieved. Similarly, the elucidation of the cellular signal transduction mechanisms beginning with the apoptosis inducing agent and leading to endonuclease activation have not been determined.

Therefore, it would be useful to provide compositions and methods for modulating cell growth and proliferation by regulation of the apoptotic signaling pathway. The compositions would have particular therapeutic utility where cell growth or proliferation is aberrant, for example, as anti-neoplastic agents. The present invention solves these and other related needs.

SUMMARY OF THE INVENTION

The present invention describes a mammalian protease capable of inducing apoptotic DNA fragmentation. The protease is found in elevated levels in mammalian tumor cells treated with apoptosis inducing agents. The protease has activity against an elastase-like substrate MAAPV.

One aspect of the invention is a ligand capable of binding a mammalian protease of 24 kDa having the amino acid composition of Table 5.

Another aspect of the invention is a method for isolating ligands of a mammalian protease of 24 kDa having the amino acid composition of Table 5, comprising screening a peptide library for peptides which bind the protease, wherein the protease is immobilized.

Another aspect of the invention is a method for identifying an inhibitor of a mammalian protease of 24 kDa having the amino acid composition of Table 5, comprising screening a library of candidate inhibitors for an ability to inhibit proteolytic activity of the protease on a substrate.

Another aspect of the invention is a method for identifying an inhibitor of a mammalian protease of 24 kDa having the amino acid composition of Table 5, comprising screening a library of candidate inhibitors for an ability to inhibit DNA fragmentation induced by the protease.

Another aspect of the invention is a method for identifying an inhibitor of a mammalian protease of 24 kDa having the amino acid composition of Table 5, comprising screening a library of candidate inhibitors for an ability to inhibit trypan blue uptake in cells, wherein the cells have been exposed to TNF, UV light, or anti-Fas antibodies.

Another aspect of the invention is a method for identifying an inhibitor of a mammalian protease of 24 kDa having the amino acid composition of Table 5, comprising screening a library of candidate inhibitors for an ability to inhibit $^{51}Cr$ release in cells, wherein the cells have been exposed to TNF, UV light, or anti-Fas antibodies.

BRIEF DESCRIPTION OF THE DRAWINGS

FIG. 1A shows the fragmentation inhibition of DK120 (carbobenzoxy-ala-ala-borophe) and TPCK to TNF, and FIG. 1B shows the fragmentation inhibition of DK120 and TPCK to UV light.

In FIG. 2, U937 cells were pretreated with and without TPCK 10 μM for 30 min, exposed to UV light 0.15 J/cm$^2$, incubated another 2.5 h, then the DNA extracted and analyzed by agarose gel electrophoresis. Lane 1 of FIG. 2 contains molecular weight markers, lane 2 contains untreated U937, lane 3 contains U937 treated with TPCK, lane 4 contains U937 treated with UV light, lane 5 contains U937 treated with TPCK and UV light.

FIG. 3A shows the OD of cell lysates from normal U937 cells, and FIG. 3B shows the OD of cell lysates from UV-light pretreated cells. FIG. 3C shows a leukocyte elastase dose response curve, in which each fraction was assayed for protease activity against the MAAPV substrate.

FIG. 4A shows active fractions of protease purified from normal U937 cells, and FIG. 4B shows active fractions of protease purified from UV light treated U937 cells.

FIG. 6A shows % DNA fragmentation by pooled protease preparations in U937 nuclei, together with commercially available proteases. FIG. 6B shows the % DNA fragmentation by the protease pool isolated from UV-treated cells, in the presence of 50 $\mu$M of protease inhibitors TPCK and DK120.

DESCRIPTION OF THE PREFERRED EMBODIMENT

Definitions

Figure 1:
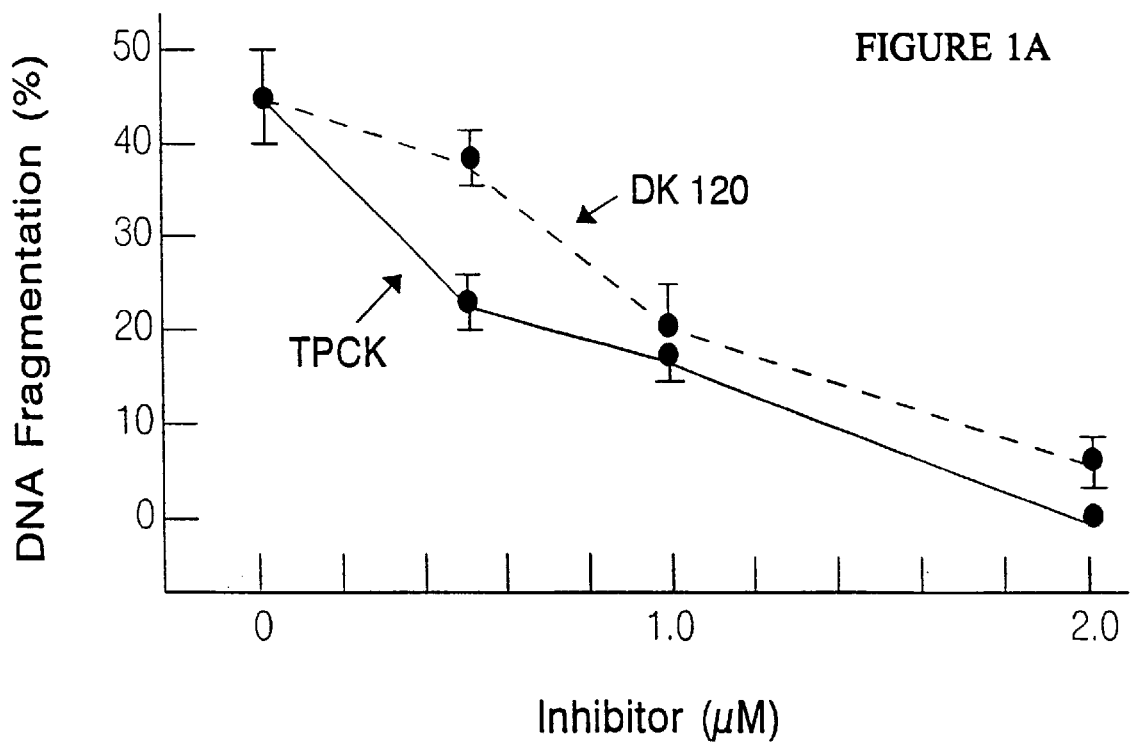
FIG. 1 comprises FIG. 1A and FIG. 1B and shows the inhibition of DNA fragmentation induced by TNF and UV light by serine protease inhibitors.
Figure 1:
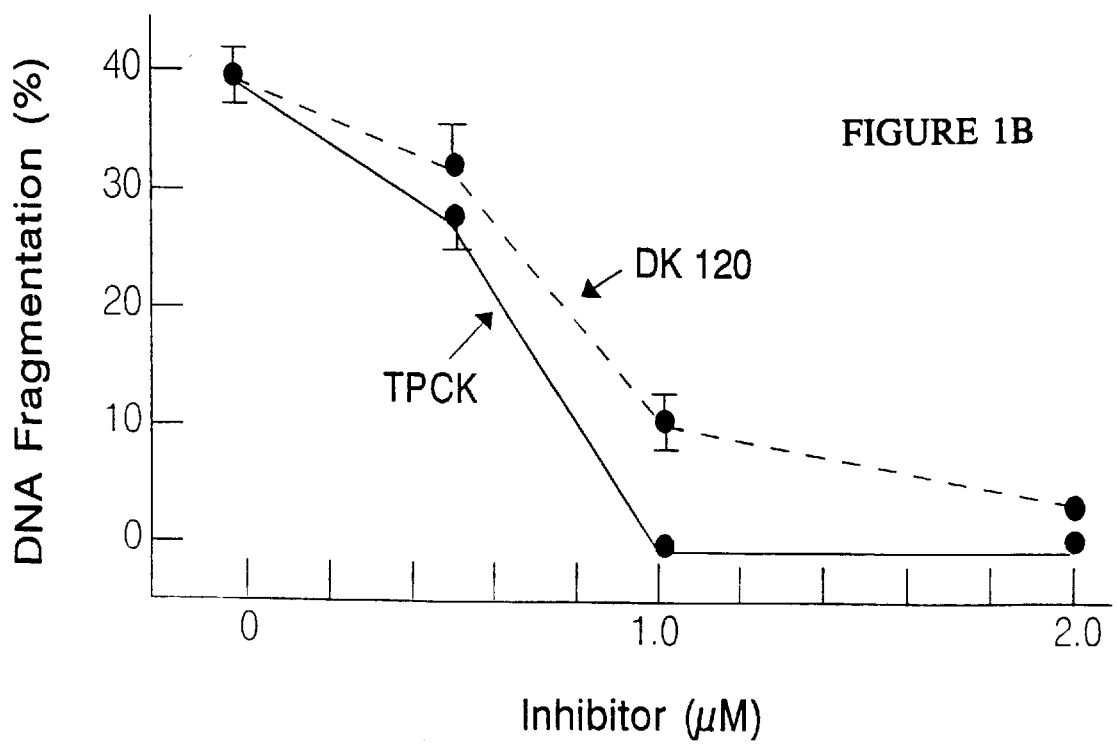

Generally, the nomenclature used hereafter, and the laboratory procedures in cell culture and protein biochemistry are those well known and commonly employed in the art. Generally, enzymatic reactions and column chromatography are performed according the manufacturer's specifications. Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For the purposes of the present invention, the foregoing terms are defined below.

The terms "therapeutically effective level" or "therapeutically effective dose" as used herein mean the minimum blood level of drug required to achieve a therapeutic effect. The terms "prophylactically effective dose" or "prophylactically effective level" as used. herein mean the minimum blood level of drug required to achieve a prophylactic effect. In prophylactic applications, compositions containing the compounds of the invention are administered to a patient susceptible to or otherwise at risk of a particular disease. In therapeutic applications, compositions are administered to a patient already suffering from a disease, in an amount sufficient to cure, ameliorate, or at least partially arrest the symptoms of the disease, or complications arising therefrom.

The terms "pharmaceutically acceptable" or "therapeutically acceptable" refer to a substance which does not interfere with the effectiveness or the biological activity of the active ingredients and which is not toxic to the host or the patient.

The terms "encoding" or "encodes" refer generally to the sequence information being present in a translatable form, usually operably linked to a promoter. A sequence is operably linked to a promoter when the functional promoter enhances transcription or expression of that sequence. An anti-sense strand is considered to also encode the sequence, since the same informational content is present in a readily accessible form, especially when linked to a sequence which promotes expression of the sense strand. The information is convertible using the standard, or a modified, genetic code. See, e.g. Watson et al., (1987) *The Molecular Biology of the Gene*, (4th Edition), Vols. 1 & 2, Benjamin, Menlo Park, Calif.

As used to refer to nucleic acid sequences, the term "homologous" indicates that two or more nucleotide sequences share a majority of their sequence. Generally, this will be at least about 700% of their sequence and preferably at least 95% of their sequence. Another indication that sequences are substantially identical is if they hybridize to the same nucleotide sequence under stringent conditions (see, e.g., Sambrook et al., *Molecular Cloning—A Laboratory Manual*, Cold Spring Harbor Laboratory, Cold Spring Harbor, N.Y., 1985). Stringent conditions are sequence-dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is at least about 0.2 molar at pH 7 and the temperature is at least about 60° C.

As used to refer to proteins or polypeptides, the term "homologous" is meant to indicate two proteins or polypeptides share a majority of their amino acid sequences. Generally, this will be at least 90% and usually more than about 95%. Homology for polypeptides or proteins is typically measured using sequence analysis software, see e.g. Sequence Analysis Software Package of the Genetics Computer Group, University of Wisconsin Biotechnology Center, 1710 University Avenue, Madison Wis. 53705. Protein analysis software matches similar sequences using measure of homology assigned to various substitutions, deletions, and other modifications. Conservative substitutions typically include substitutions within the following groups glycine, alanine; valine, isoleucine, leucine; aspartic acid, glutamic acid; asparagine, glutamine; serine, threonine; lysine, arginine; and phenylalanine, tyrosine.

The term "isolated" as applied to nucleic acids, means a nucleic acid substantially separated from other macromolecules, cellular components, or DNA sequences which naturally accompany a native nucleic acid, e.g. ribosomes, polymerases, other nucleic acid sequences, and the like. The term includes a nucleic acid that has been removed from its naturally occurring environment, and includes recombinant or cloned DNA isolates and chemically synthesized analogues, and analogues biologically synthesized by heterologous systems. A substantially pure or biologically pure nucleic acid includes isolated forms of the nucleic acid.

The phrase "biologically pure" or "substantially pure" refers to material that is substantially or essentially free from components which normally accompany it as found in its native state.

The term "recombinant" refers to a nucleic acid sequence which is not naturally occurring, or is made by the artificial combination of two otherwise separated segments of sequence, i.e. by chemical synthesis, genetic engineering, and the like.

The present invention examines the role of proteases in signal transduction leading to DNA fragmentation and apoptosis. It has been surprisingly discovered that certain inhibitors of serine proteases block TNF or UV light-induced apoptosis in tumor cell lines. A 24 kDa protease has been purified that was activated by UV light in U937 cells and induced DNA fragmentation in isolated nuclei.

The intracellular apoptotic events and mechanism may differ depending on the cell type and inducing agent. Some examples of apoptosis require new gene expression and protein synthesis, as described for example, in Cohen J. J., et al. (1984) *J. Immunol.* 132, 38–42, Ucker, D. S., et al. (1989) *J. Immunol.* 143, 3461–3469, and Sellins, K. S., et al. (1987) *J. Immunol.* 139, 3199–3209. In other apoptotic examples, gene expression and protein synthesis are not required, as described in Duke, R. C., et al., (1983) *Proc. Natl. Acad. Sci.* 80, 6361–6365, and Martin, S. J., et al. (1990) *J. Immunol.* 145, 1859–1867. Differences have also been reported in the requirement for extracellular calcium, Cohen J. J., et al., (1984) *J. Immunol.* 132, 38–42; Kyprianou, N., et al., (1988) *Prostate* 13, 103–117; McConkey, D. J., et al., (1990) *FASEB J.* 4, 2661–2664; and Alnemri, E. S., et al., *J. Biol. Chem.* 265, 17323–17333.

Both TNF and UV light act as apoptosis inducing agents in many cell types and suggest that both agents stimulate signals converging to a final common pathway leading to DNA fragmentation. This process does not require protein synthesis or extracellular calcium, Hasegawa, Y., et al. (1989) *J. Immunol.* 142, 2670–2676. Phorbol myristate acetate (PMA) inhibits apoptosis induced by TNF or UV light, suggesting a regulatory role for PKC, in agreement with other examples of apoptosis described in Kanter, P., et al., (1984) *Biochem. Biophys. Res. Commun.* 118, 392–399; Rodriguez-Tarduchy, G., et al. (1989) *Biochem. Biophys. Res. Commun.* 164, 1069–1075; Lucas, M., et al. (1990) *FEBS Lett.* 279, 19–20; McConkey, D. J., et al. (1989) *J. Biol. Chem.* 264, 13399–13402; and McConkey, D. J., et al. (1991) *J. Immunol.* 146, 1072–1076.

Augmentation of intracellular protein phosphorylation by inhibitors of serine/threonine-dependent phosphatases promoted TNF-induced apoptosis and overcame the resistance of a variant of the human histiocytic lymphoma cell line U937, as described in Wright, S. C., et al. (1993) *J. Cell. Biochem.* 53: 222–233, suggesting a critical role for protein kinases in signal transduction, although no specific kinase has been identified.

Apoptosis in U937 cells is also blocked by 3-aminobenzamide, an inhibitor of poly ADP-ribose polymerase (pADPRp). Furthermore, increased levels of pADPRp activity have been measured in lysates of TNF or UV light-treated U937 cells. These findings are in agreement with other reports of activation of pADPRp in cells in response to TNF, as described in Agarwal, S., et al. (1988) *J. Immunol.* 140, 4187–4192. Whether this enzyme functions to activate endonucleases or contributes to cell death through depletion of NAD, as described in Berger, N. A., (1985) *Radiation Research* 101 4–15, and Carson, D. A., et al. (1986) *Exp. Cell. Res.* 164 273–281, has not yet been established.

The present invention provides a protease which is involved in the apoptotic signaling pathway in human U937 tumor cells. Two inhibitors of serine proteases, TPCK and DK120, suppressed DNA fragmentation in the U937 histiocytic lymphoma in response to either TNF or UV light as well as UV light-induced DNA fragmentation in the BT-20 breast carcinoma, HL-60 myelocytic leukemia, and 3T3 fibroblasts. The protease was purified by affinity chromatography with DK120 as ligand and showed high activity on a synthetic substrate preferred by elastase-like enzymes (ala-ala-pro-val) (SEQ ID NO: 1), but showed little or no activity against a trypsin substrate, BLT. Induction of apoptosis correlated with a 10 fold increase in the activity of the DK120-binding protease purified from UV-treated U937 as compared to recovery from normal cells. Further purification to homogeneity by subsequent heparin-Sepharose affinity chromatography followed by reverse phase HPLC revealed a single band of 24 kDa on a silver stained SDS gel. In addition to protease activity, the purified enzyme induced DNA fragmentation in isolated U937 nuclei. Thus, the 24 kDa protease transmits signals leading to DNA fragmentation in U937 cells undergoing apoptosis.

Thus, the present invention provides a protease having a role in the signaling pathways leading to apoptosis. The role of the protease was observed by testing the effects of a variety of protease inhibitors on DNA fragmentation induced by TNF or UV light in an apoptotic cell line. The regulation and modulation of apoptosis was examined using primarily the human histiocytic lymphoma cell line U937 as a model system. This cell line undergoes apoptosis in response to a variety of apoptotic inducing agents, including tumor necrosis factor alpha (TNF), UV light, heat shock, oxidative stress, and chemotherapeutic drugs, as described in Wright, S. C., et al. (1992) *J. Cell. Biochem.* 48, 344–355, Wright, S. C., et al. (1993) *FASEB J.* 7, 1045–1051. As used herein, "apoptosis inducing agent" includes any biological, chemical, biochemical or physical means of inducing a complete or partial apoptotic response in a target cell. Target cells may be normal cells, or cells having aberrant growth or proliferation, such as tumor cells. Most nucleated eukaryotic cells tested have shown the capacity to undergo apoptosis in response to appropriate stimuli, including non-mammalian cells such as avian and nematode. An analogous process has not been demonstrated in prokaryotes.

Examples of apoptosis inducing agents include UV light, hyperthermia or heat shock, calcium, ATP, actinomycin D, A23187 $Ca^{2+}$-$Mg^{2+}$ ionophore, cytochalasin B, cycloheximide, anti-CD3/T-cell receptor antibodies, epipodophyllotoxins, gliotoxin, glucocorticoids, lymphotoxins, RU486, TCDD, TGF-β1, oxidative stress, viral infections, chemotherapeutic drugs, cold shock, gamma radiation, cisplatin, etoposide, teniposides, DNA alkylating agents, macromolecular synthesis inhibitors, immunological agents such as natural killer cells, effector cells, lymphotoxins, K cells, T cells, and the like, and others, as described for example in Green, D. R. et al., Apoptosis and Cancer, in Principles and Practice of Oncology Updates Volume 8, J. B. Lippincott Company, January 1994 Number 1, and Gerschenson, L. E., et al. (1992) *FASEB J.* 6:2450–2455.

Two serine protease inhibitors, TPCK and DK120, have been found to be especially potent inhibitors of apoptotic DNA fragmentation, as shown in FIG. 1. U937 cells were pretreated with the indicated concentrations of inhibitors for 1 hr, then exposed to either TNF 1.0 ng/ml plus cycloheximide 0.5 μg/ml (FIG. 1A) or WV light at 0.1 J/cm² (FIG. 1B), dosages in the linear portion of the dose response curve. After incubating for 1.5–2 h, assays were harvested and % DNA fragmentation was determined. As seen in FIG. 1, both DK120 and TPCK could dose-dependently inhibit DNA fragmentation with maximum suppression occurring at 2.0 µM in this experiment. TPCK is a potent inhibitor of chymotrypsin-like enzymes, whereas DK120 is a boronic acid-containing tripeptide substrate analog that also potently inhibits chymotrypsin-like enzymes, Kinder, D. H., et al. (1985) *J. Med. Chem.* 28, 1917–1925, and Kinder, D. H. et al. (1991) *Invasion and Metastasis* 12:309–319.

Figure 2:
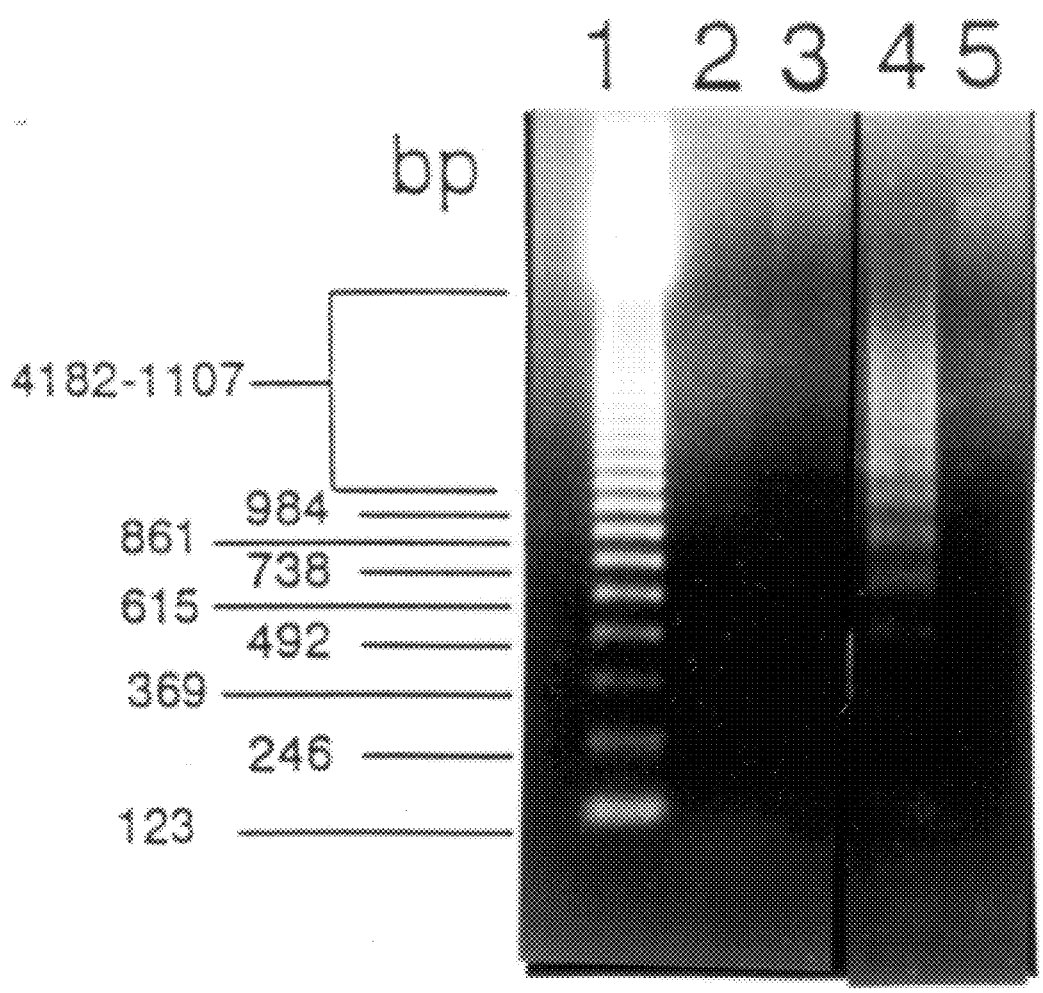
FIG. 2 shows the inhibition of DNA fragmentation by TPCK as shown by agarose gel electrophoresis.

Inhibition of apoptotic DNA fragmentation by TPCK was confirmed by agarose gel electrophoresis as shown in FIG. 2. DNA from untreated U937 cells (lane 2) or cells treated with TPCK alone (lane 3) showed no DNA fragments. Exposure of U937 cells to UV light resulted in the appearance of DNA fragments in multiples of 180 base pairs, typical of apoptosis (lane 4). However, pretreatment with TPCK completely abolished UV light-induced DNA fragmentation (lane 5).

To further characterize the protease activity involved in apoptosis, the effects of a panel of compounds on both TNF and UV light-induced apoptosis of U937 cells was tested. All compounds were used at nontoxic concentrations for the duration of the assay as determined by trypan blue exclusion. The $IC_{50}$ values of active inhibitors as well as the highest nontoxic concentration of inactive compounds tested are provided in Table 1.

E64 and N-ethylmaleimide, and the aminopeptidase inhibitor, bestatin, were inactive. Negative results may be inconclusive since they may be due to a) inefficient penetration of the inhibitor to the presumably intracellular site of protease action or b) cellular toxicity at effective inhibitor concentrations.

To determine if these findings were unique to U937 or if other cell lines also require protease activity to undergo apoptosis, the effects of several inhibitors on apoptosis induced by UV light in the human mammary carcinoma, BT-20, the murine fibroblast cell line, 3T3, and the human myeloid leukemia, HL-60 were tested. For the BT-20 and 3T3 cells, target cells were pretreated for one hour (with or without inhibitors as indicated in the table) and exposed to UV light at 0.5 $J/cm^2$ and then incubated for eight hours prior to assessing DNA fragmentation. HL-60 cells were pretreated for one hour (with or without inhibitors as indicated in the table) and exposed to UV at 0.2 $J/cm^2$ and then incubated for two hours prior to assessing DNA fragmentation.

TABLE 1

Effect of Protease Inhibitors on TNF and UV-Light Induced Apoptosis

| Inhibitor | Target Protease | Active Concentration | Inactive Compounds Highest Concentration Tested |
|---|---|---|---|
| TPCK (N-1-tosylamide-2-phenylethylchloromethyl ketone) | Serine/Chymotrypsin | 2.0 µM | |
| APNE (N-acetyl-DL-Phenylalanine β-naphthyl ester) | Chymotrypsin | 40 µM | |
| DK120 | Serine/Chymotrypsin | 1.2 µM | |
| IBA (isopropylboronic acid) | None | | 20 µM |
| TLCK (N-α-p-tosyl-L-lysine-chloromethyl ketone) | Serine/Trypsin | | 50 µM |
| TAME (p-toluene-sulfonyl-L-arginine methyl ester) | Trypsin | | 100 µM |
| PMSF (phenylmethylsulfonylfluoride) | Serine | | 100 µM |
| Chymostatin | Serine | | 100 µM |
| DFP (diisopropylfluorophosphate) | Serine | | 100 µM |
| Benzamidine | Serine | | 100 µM |
| Leupeptin | Serine Some cysteine | | 100 µM |
| E64 | Cysteine | | 100 µM |
| N-ethylmaleimide | Cysteine | | 20 µM |
| Bestatin | Aminopeptidase | | 100 µM |

In addition to TPCK and DK120, APNE, a chymotrypsin pseudosubstrate, also blocked DNA fragmentation. However, not all inhibitors of serine proteases were active since TLCK, TAME, PMSF, chymostatin, DFP, benzamide, and leupeptin were without effect. IBA is a boronic acid analog devoid of protease inhibitory activity which does not inhibit DNA fragmentation, indicating that the inhibition by DK120 is not a nonspecific effect of any boron compound. In addition, the inhibitors of sulfhydryl dependent enzymes,

TABLE 2

Inhibition of DNA Fragmentation by Protease Inhibitors in Several Tumor Cell Lines

| | Target Cells | | |
|---|---|---|---|
| Inhibitor | BT-20 | 3T3 | HL-60 |
| — | 44 ± 3.6 | 38 ± 1.9 | 49 ± 2.0 |
| TPCK 5 µM | 0 ± 0 | 18 ± 0.8 | 1 ± 2.3 |
| TPCK 1 µM | 19 ± 5.5 | 32 ± 1.1 | 19 ± 2.0 |
| DK 120 5 µM | 0 | 19 ± 1.9 | |
| DK 120 1 µM | 0 | 24 ± 0.3 | |

TABLE 2-continued

Inhibition of DNA Fragmentation by Protease Inhibitors in Several Tumor Cell Lines

| Inhibitor | Target Cells | | |
|---|---|---|---|
| | BT-20 | 3T3 | HL-60 |
| DK 120 0.2 μM | 5 ± 8.7 | | |
| DFP 100 μM | 43 ± 1.9 | | |
| E64 100 μM | 41 ± 5.6 | 42 ± 2.7 | |
| Leupeptin 100 μM | 42 ± 5.6 | 36 ± 2.6 | |

Table 2 shows that both TPCK and DK120 effectively blocked DNA fragmentation, whereas DFP, E64, and leupeptin were inactive. Taken together, these results indicate that the activity of a serine protease is essential for at least one apoptotic pathway operating in different cell types responding to different stimuli.

To purify the apoptotic protease, a DK120 affinity column was prepared. The matrix efficiently bound commercially available chymotrypsin, which could be eluted with 0.1 M HCl. After neutralization, the eluted material still exhibited high levels of protease activity measured on the chymotrypsin substrate succinyl-ala-ala-pro-phe-p-nitroanilide (SEQ ID NO: 2) (SAAPP) substrate.

Figure 3:
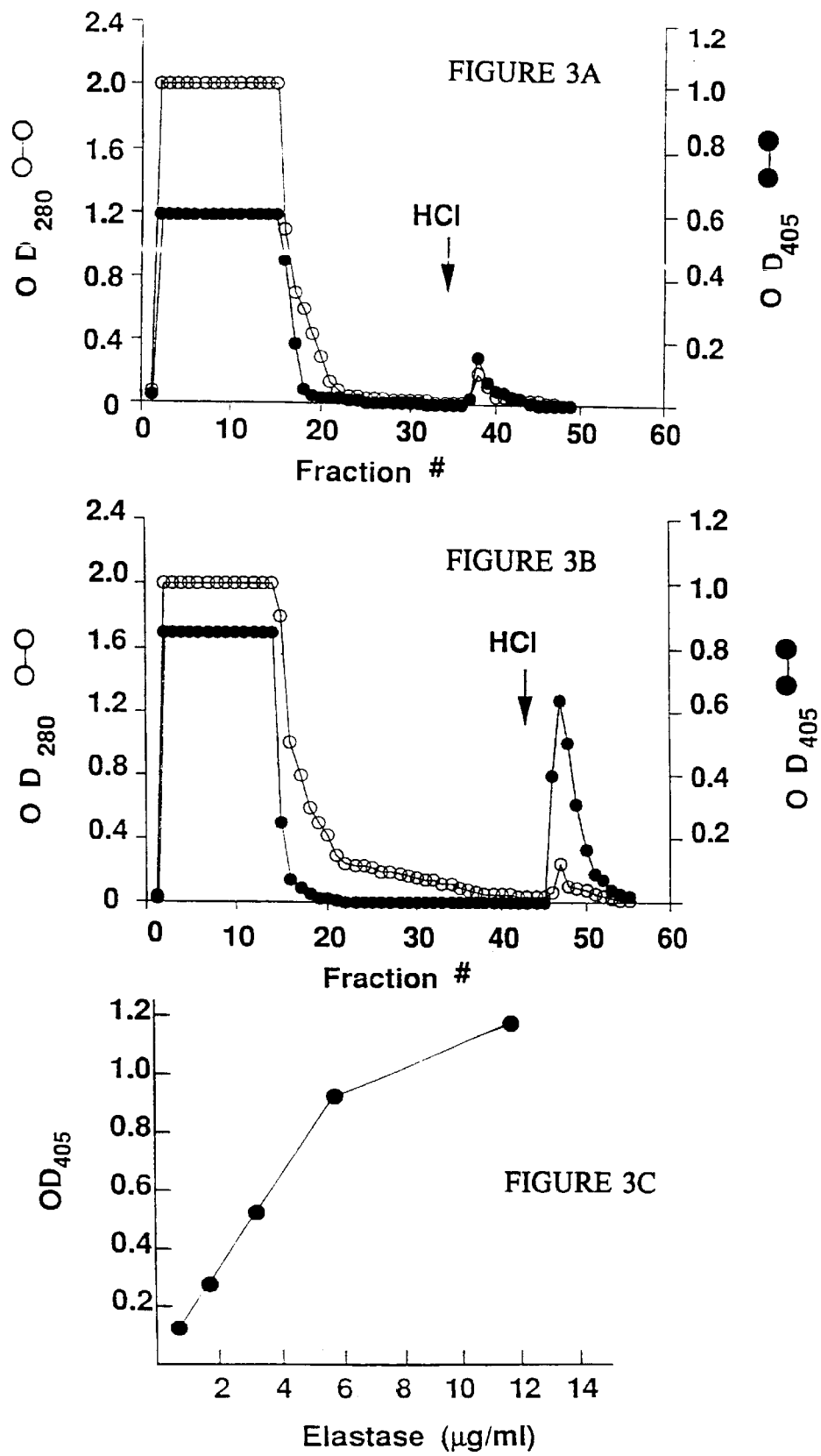
FIG. 3 comprises FIGS. 3A, 3B, and 3C, and shows the DK120 affinity purification of the 24 kDa U937 protease. OD measured at 280 nm reflects total protein content, whereas OD at 405 nm measures protease activity on the MAAPV substrate.

To prepare starting material, U9:37 cells were exposed to UV light (0.2 J/cm²) and incubated at 37° C. until approximately 50–70% of the cells exhibited the apoptotic morphology (this usually required 1.5–2 hr. incubation). Numerous cytoplasmic membrane blebs characteristic of apoptosis were easily discernable by light microscopy, see Wright, S. C., et al. (1992) *J. Cell. Biochem.* 48, 344–355. Cells were harvested at this time point while they were ≧95% viable by trypan blue exclusion. However, 90–100% of the cells were destined to die if the incubation was continued another 2–3 hr. Cytoplasmic extracts were prepared from apoptotic as well as normal untreated U937 cells. Material from equal numbers of control and UV light treated cells containing equal amounts of protein were chromatographed in an identical fashion on DK120 affinity columns. The results in FIG. 3 show the vast majority of the protein as detected by absorption at 280 nm passed through the column in the unbound fractions #2–17, whereas a relatively small amount of material eluted with 0.1 M HCl. Proteolytic activity present in the eluted fractions was tested using several different synthetic substrates. The eluate from UV irradiated cells showed high proteolytic activity against the elastase substrate methoxysuccinyl-ala-ala-pro-val-p-nitroanilide (SEQ ID NO: 3) (MAAPV), but relatively low activity against the trypsin substrate, N-α-benzyloxycarbonyl-L-lysine thiobenzyl ester (BLT). The eluate from the control cells showed low activity against both substrates. Therefore, proteolytic activity was monitored during protein purification using the MAAPV substrate. To maximize sensitivity, this assay was carried out at room temperature for 20 hr. However, the dose response using commercially available leukocyte elastase was still linear up to an OD of 1.0 even at this prolonged incubation time (FIG. 3C).

The profiles of protease activity tested in all the column fractions demonstrate high levels of activity in the unbound fractions. However, when the flow-through fractions were pooled and re-applied to the DK120 column, all protease activity was still found in the unbound fractions and not in the eluate. Thus, lysates from both control and UV treated U937 cells contain substantial amounts of proteases that do not bind to the DK120 column.

Figure 4:
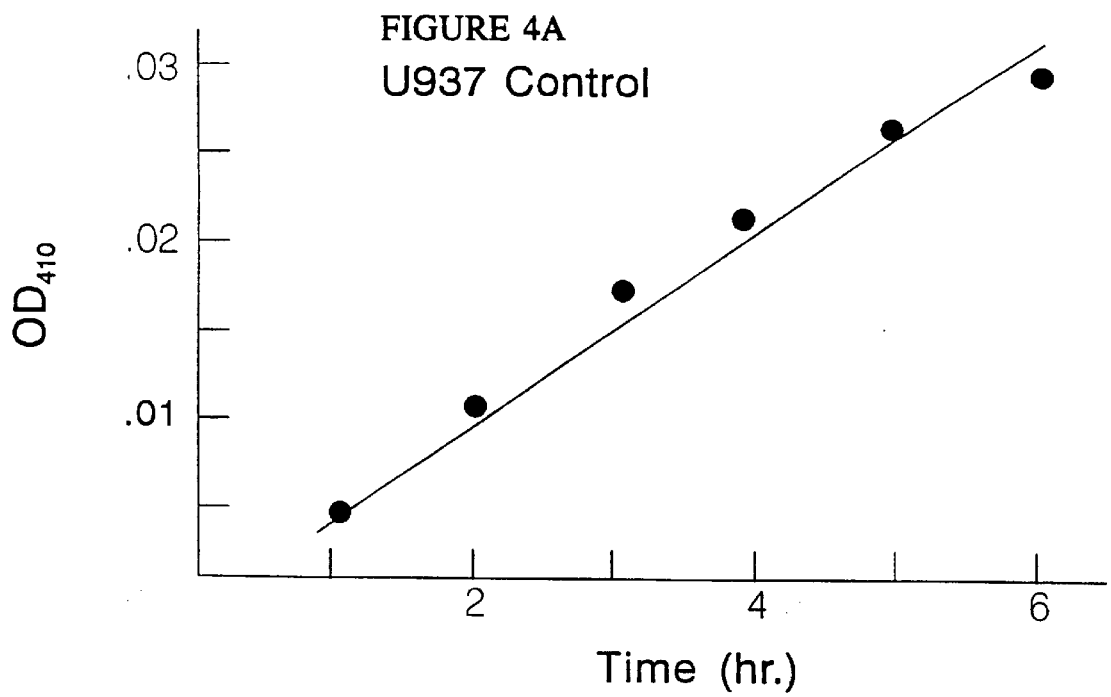
FIG. 4 comprises FIG. 4A and FIG. 4B and shows a kinetic protease assay to quantitate DK120-binding protease activity against the MAAPV substrate.
Figure 4:
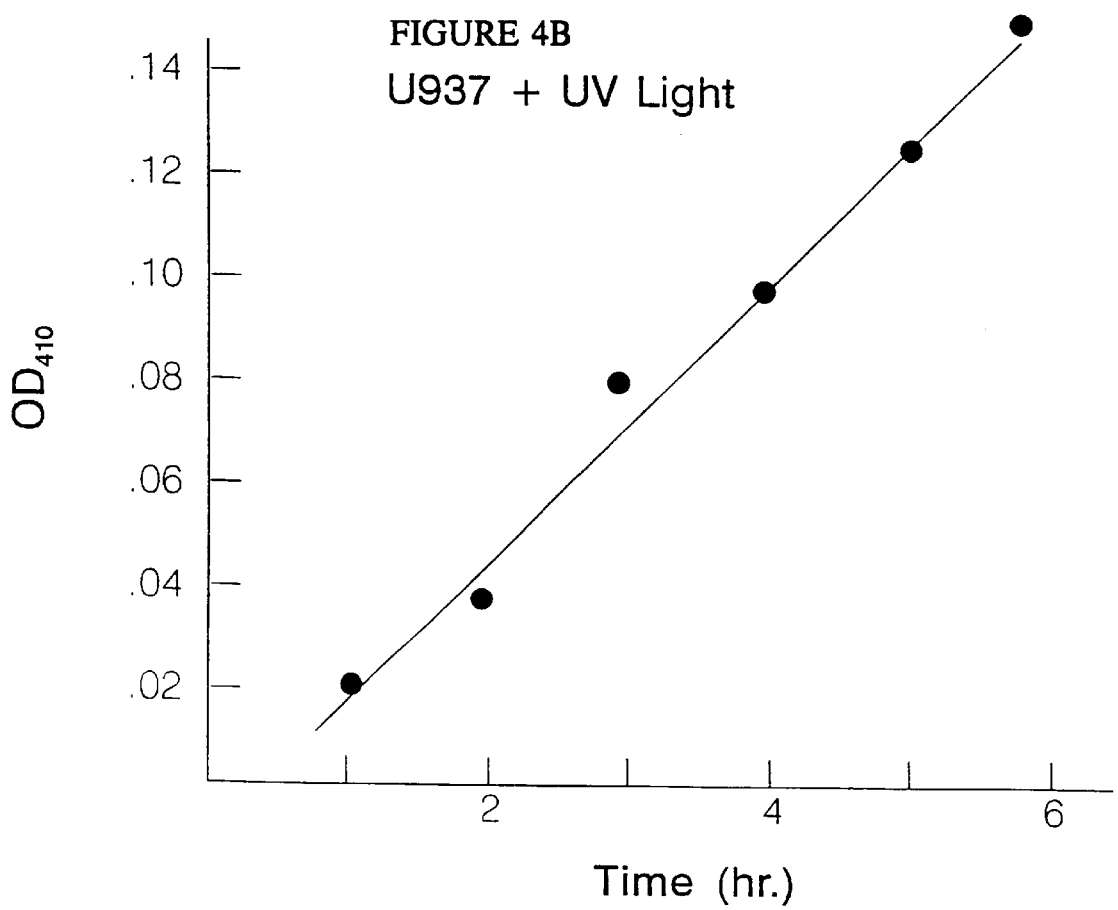

The protease activity profiles suggest that enzyme activity in the eluate from UV treated cells is significantly increased over that recovered from control cells. To quantitate activity, the active eluted fractions from each column were pooled separately and tested in a kinetic assay. The results in FIG. 4 show a linear increase in optical density monitored from 1–6 hr. Units of enzyme activity calculated as described in Example 7 revealed a total recovery of 27.8 U from control cells versus 248 U from UV treated cells. These results indicate that UV treatment causes almost a 10 fold increase in the activity of DK120-binding enzymes. No UV-activated protease could be isolated from Sepharose 6B control columns, indicating that this enzyme does not nonspecifically bind to the unconjugated resin.

Figure 5:
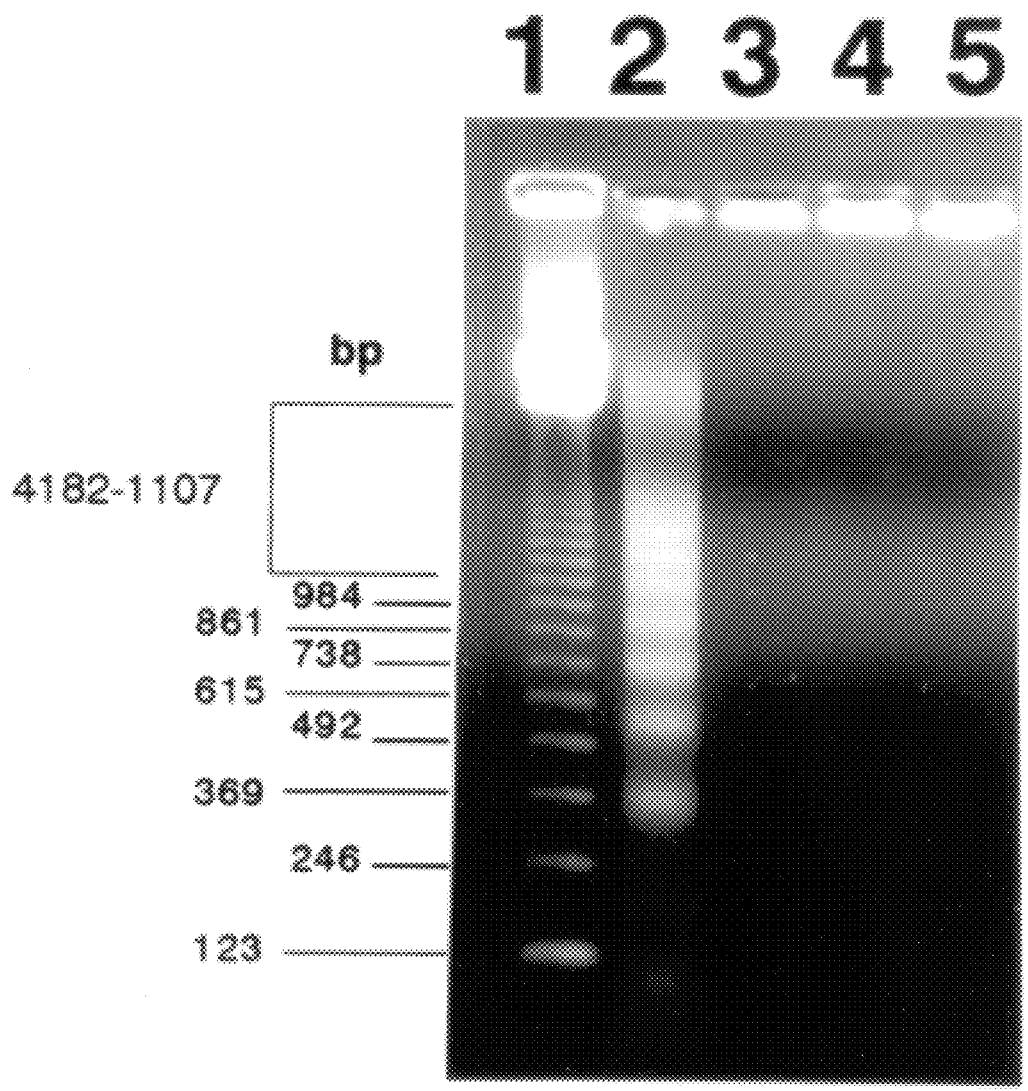
FIG. 5 shows the visualization of DNA fragmentation by endonuclease activity in isolated nuclei. Lane 2 shows apoptotic DNA fragmentation in response to incubation with the protease of the present invention. The sample of Lane 3 was pre-treated with alphal-anti-protease. Lane 4 and 5 show the DNA treated with alphal-anti-protease alone, or untreated, respectively. Size markers (in base pairs) are provided in lane 1.

Gel electrophoresis was employed to test the ability of the semi-purified protease to generate apoptotic endonuclease DNA cleavage. During apoptosis, endonucleases cleave DNA in the linker regions to release fragments in multiples of 180 base pairs. DNA was extracted from isolated nuclei after exposure to DK120 affinity-purified protease obtained from U937 cells exposed to UV light. The results in FIG. 5 show that isolated nuclei incubated with the semi-purified protease released internucleosomal-sized DNA fragments to produce the electrophoretic "ladder" pattern typical of apoptosis (FIG. 5, lane 2). However, if the protease preparation was pretreated with α1-anti-protease for 1 hr. prior to adding to the nuclei, DNA fragmentation was abolished (FIG. 5, lane 3). The DNA from untreated nuclei (lane 5) or from nuclei treated with α1-anti-protease alone (lane 4) remained in high molecular weight form. These results confirm that a DK120-binding protease can activate internucleosomal DNA cleavage in isolated U937 nuclei.

Figure 6:
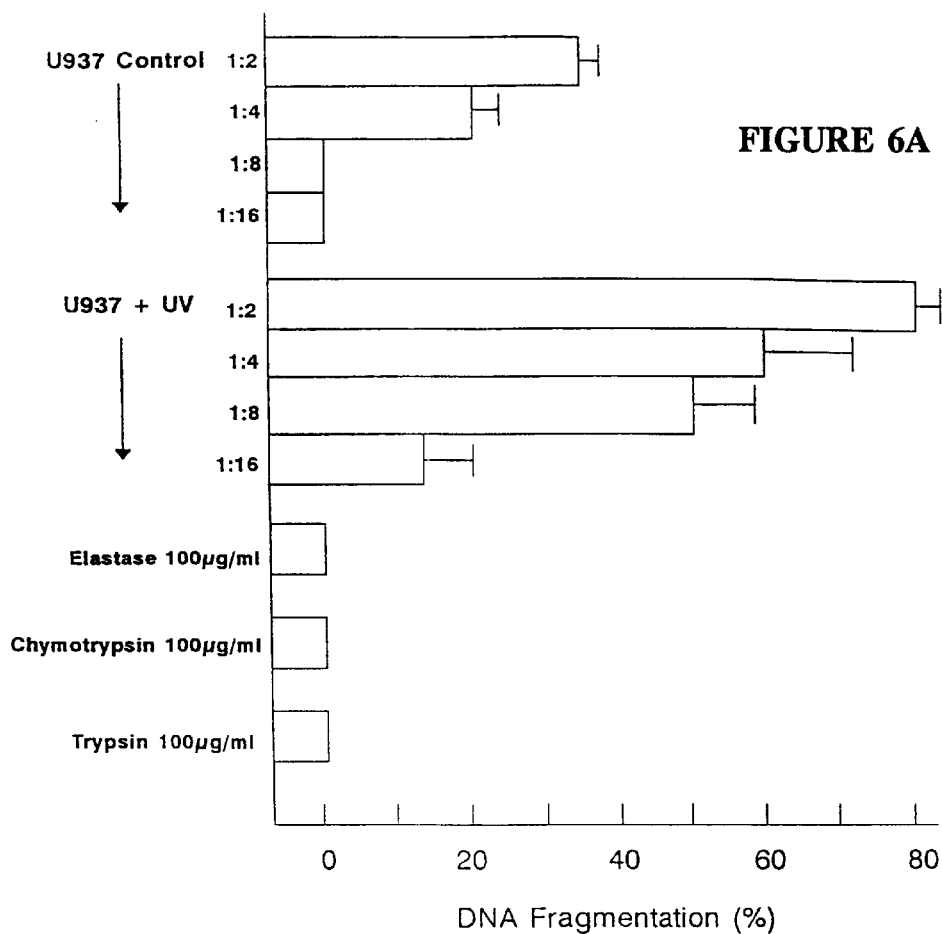
FIG. 6 comprises FIG. 6A and FIG. 6B and shows activation of DNA fragmentation in isolated nuclei by semi-purified protease fractions.
Figure 6:
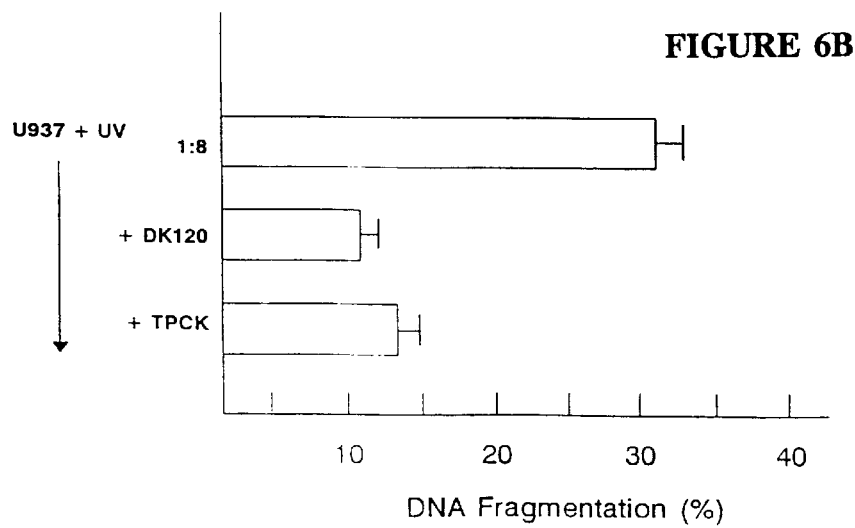

To further examine their role in apoptosis, the two pools of semi-purified protease were tested for their effects on isolated U937 nuclei. The results in FIG. 6A show that both pools caused DNA fragmentation, although the pool derived from UV treated cells had much higher activity than that from control cells. In contrast, elastase, chymotrypsin, and trypsin tested at concentrations as high as 0.1 mg/ml were completely inactive. Furthermore, the nuclear DNA fragmenting activity of protease isolated from UV-treated cells was inhibited by DK120 and TPCK, as shown in FIG. 6B. This suggests that the semi-purified protease may directly or indirectly activate a nuclease endogenous to U937 nuclei. Alternatively, the protease may modify chromatin structure to make the DNA more susceptible to digestion by a nuclease that may contaminate the protease preparation. This possibility was tested by incubating both pools with naked DNA isolated from U937 cells. DNase activity was measured using purified U937 DNA as a substrate as described in Example 6.

TABLE 3

Semi-Purified Protease Preparations Do Not Have DNase Activity

| Sample | % DNA Fragmentation |
|---|---|
| U937 Control Protease | 0 |
| UV-Activated U937 Protease | 0 |
| DNase 1 1.0 ng/ml | 61 |
| DNase 1 0.1 ng/ml | 29 |
| DNase 1 0.01 ng/ml | 11 |
| Micrococcal Nuclease 50 U/ml | 72 |
| Micrococcal Nuclease 10 U/ml | 65 |
| Micrococcal Nuclease 2 U/ml | 50 |
| Micrococcal Nuclease 0.4 U/ml | 0 |

The results shown in Table 3 indicate that neither pool could digest DNA, in contrast to the commercially available nucleases tested in parallel. The sensitivity of the assay is demonstrated by the fact that DNase I at only 0.1 ng/ml and micrococcal nuclease at 2 U/ml gave clearly detectable signals. Therefore, it is unlikely that a contaminating nuclease accounts for the ability of the protease preparations to activate DNA fragmentation in isolated nuclei. In order to determine if the DNA fragmenting activity is mediated by the DK120-binding protease, this enzyme was purified to homogeneity and tested.

Figure 7:
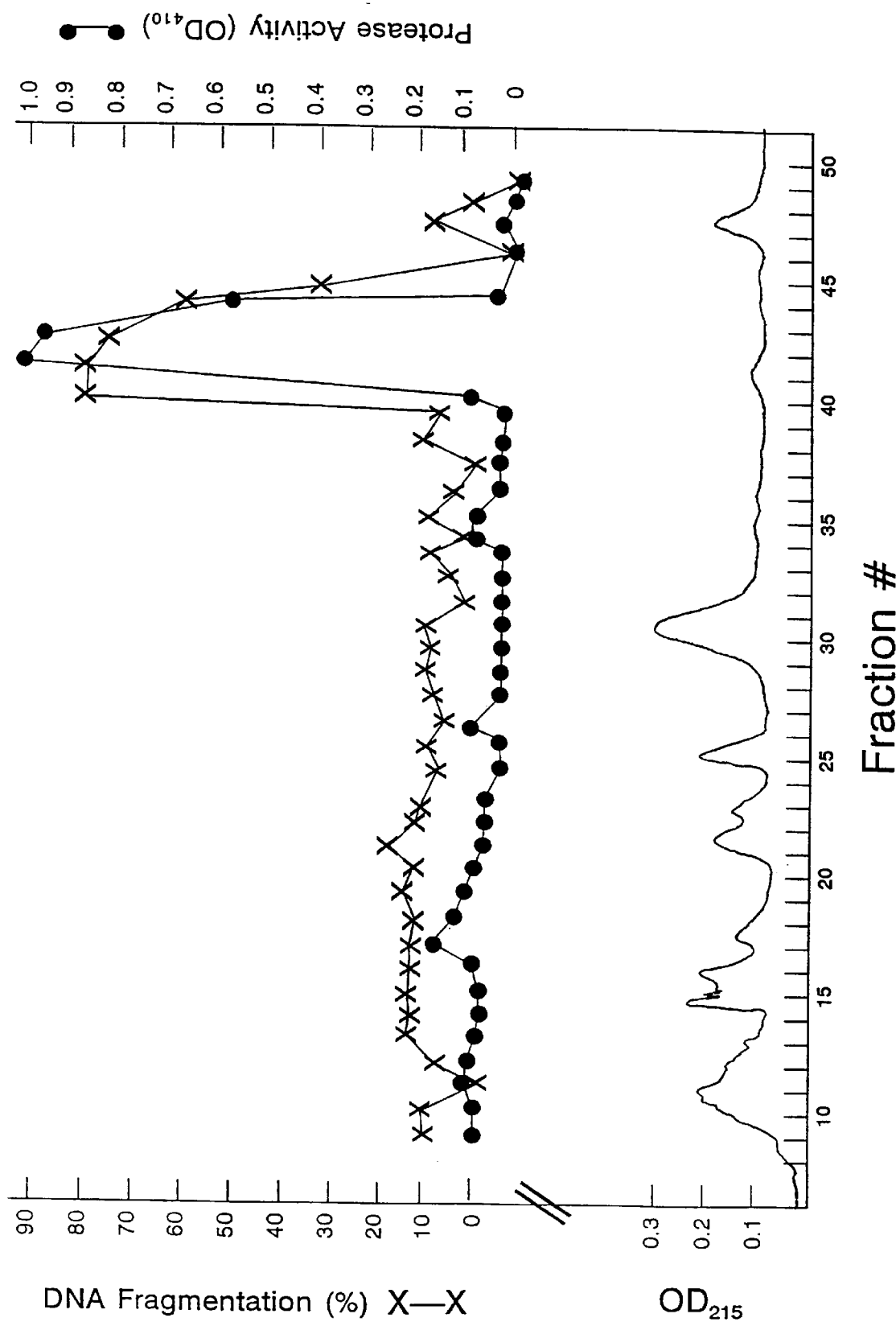
FIG. 7 shows the purification of U937 protease by reverse phase HPLC and demonstration of proteolytic and DNA fragmentation activity. Fraction numbers from the final purification step by reverse phase C4 HPLC are shown on the lower axis of FIG. 7. The lower tracing reflects the total protein profile as detected by absorbance at 215 nm. Percent DNA fragmentation (against isolated U937 nuclei) for each fraction is indicated by X's in FIG. 7, while protease activity against the MAAPV substrate for each fraction is indicated by solid circles.
Figure 8:
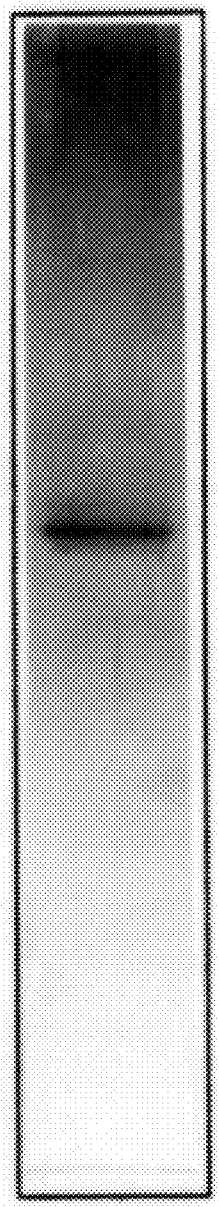
FIG. 8 is a non-reducing, silver-stained, SDS PAGE analysis of purified 24 kDa U937 protease. Molecular weight markers (in kDa) are indicated.

Protease from $5 \times 10^{10}$ U937 cells pretreated with UV light was purified by multiple separations on the DK120 affinity column. Active eluted fractions were pooled and applied to a heparin-Sepharose column. All protease activity bound to the column and was eluted with a NaCl gradient. Active fractions were further purified using an HPLC reverse phase C4 column. All fractions were tested for protease activity against MAAPV substrate as well as the ability to activate DNA fragmentation in isolated U937 nuclei. The results in FIG. 7 show that both activities co-eluted with a peak of activity in fraction 41. These fractions were inactive against the trypsin substrate, BLT. SDS PAGE analysis of fraction 41 under non-reducing conditions revealed a single band of 24 kDa by silver staining, as shown in FIG. 8. The molecular weight under reducing conditions was also 24 kDa. The purified enzyme was highly unstable, in that all activity was lost after 48 h at 4° C.

The results of the protease purification are summarized in Table 4.

TABLE 4

Purification of 24 kDa U937 Protease

| Purification Step | Total Protein (mg) | Protease Activity (U/ml) | Total Protease (U) | Specific Activity (U/mg) |
| --- | --- | --- | --- | --- |
| Cell Lysate | 245 | not determined | n.d. | n.d. |
| DK120 Affinity | 4.10 | 27.6 | 4960 | 1210 |
| Heparin Sepharose | 0.14 | 38.9 | 777 | 5557 |
| RP HPLC | 0.0018 | 95 | 507 | 28167 |

An attempt to determine the N-terminal amino acid sequence of the reverse phase purified material was unsuccessful, due to a blocked N terminus. The amino acid composition was determined at the Stanford University Medical Center Protein and Nucleic Acid Facility using a Beckman 6300 analyzer according to standard procedures, and is shown in Table 5.

TABLE 5

Amino Acid Composition

| Residue | # Residues/Molecule |
| --- | --- |
| Asx | 25 |
| Thr | 7 |
| Ser | 15 |
| Glx | 30 |
| Pro | 6 |
| Gly | 43 |
| Ala | 17 |
| Val | 16 |
| Met | 3 |
| Ile | 10 |
| Leu | 22 |
| nleu | 39 |
| Tyr | 5 |

TABLE 5-continued

Amino Acid Composition

| Residue | # Residues/Molecule |
| --- | --- |
| Phe | 8 |
| His | 7 |
| Lys | 8 |
| Trp | not determined |
| Arg | 13 |

According to the present invention, a 24 kDa protease is involved in activating DNA fragmentation in U937 cells undergoing apoptosis. Evidence for the involvement of the 24 kDa protease is: a) DNA fragmentation in U937 and several other cell lines is blocked by the protease inhibitors, TPCK and DK120, b) activation of apoptosis by UV light caused approximately a 10 fold increase in the activity of a protease isolated by binding to DK120 affinity columns, and c) purification to homogeneity revealed a single peptide of 24 kDa that had protease activity and also activated DNA fragmentation in isolated U937 nuclei.

These findings provide the basis for a model of the mechanism of apoptosis in U937 cells. We propose that normal U937 cells contain the 24 kDa protease in an inactive proenzyme form or else in an active form that is normally sequestered from its substrate. This is supported by the observation that DNA fragmentation in U937 cells triggered by TNF or UV light is not blocked by inhibitors of protein synthesis. Low levels of a DK120-binding protease were recovered from normal U937 cells. This may be due to the artifactual activation of a proenzyme during cell lysis and purification. Alternatively, it may reflect the low incidence of apoptosis occurring spontaneously in cell culture.

Agents inducing apoptosis, such as UV light, may directly or indirectly activate the 24 kDa protease. UV light can cause structural modifications in proteins, and thus may activate a latent form of the 24 kDa protease. Alternatively, UV light may inactivate a protease inhibitor that would normally function to protect a cell from apoptosis. If the UV effect is indirect, the signal could be transduced by second messengers that activate the protease (or inactivate the postulated protease inhibitor). Such signals could involve protein phosphorylation, since UV light has been shown to activate certain protein kinases participating in the UV response in other cells, Devary, Y., et al. (1992) *Cell* 71, 1081–1091, and ionizing irradiation activates protein kinases leading to apoptosis in B lymphocytes, Uckun, F. M., et al. (1992) *Proc. Natl. Acad. Sci.* 89:9005–9009. Alternatively, the UV signal may be transduced through the generation of free radicals, which modify the function of many proteins.

Once activated, the 24 kDa protease acts on a substrate located in the nucleus. One possible substrate is a fragmentation-causing endonuclease that would normally be latent in the nucleus. Alternatively, the protease may cleave other molecules that in turn activate endogenous nucleases. One possible candidate is the nuclear enzyme poly-ADP-ribose polymerase (pADPRp). This enzyme is activated in cells undergoing apoptosis and its inhibitors block DNA fragmentation in U937. pADPRp is proteolytically cleaved yielding enzymatically active fragments in cells undergoing apoptosis induced by chemotherapeutic drugs as described in Kaufmann, S. H., et al. (1993) *Cancer Res.* 53, 3976–3985.

Previous studies have observed both generalized proteolysis as well as specific proteolytic processing of precursor IL-1 in cells undergoing apoptosis (Kaufmann, S. H. (1989) *Cancer Res.* 49, 5870–5878 and Hogquist, K. A., et al. (1991) *Proc. Natl. Acad. Sci.* 88, 8485–8489). However, in these studies, experiments were not performed to address the question of whether the protease activity is an essential step in the apoptotic pathway or is just an epiphenomenon. More recently, it has been shown that overexpression of recombinant IL-1β converting enzyme (ICE) induced apoptosis in rat fibroblasts (Miura, M., et al. (1993) *Cell* 75:653–669), implicating this protease in signaling DNA fragmentation. ICE is a cysteine protease consisting of two active subunits of MW 20 and 10 kDa (Thornberry, N. A., et al. (13.92) *Nature* 356:768–774) that requires Asp at the $P_1$ site (Howard, A. D., et al. (1991) *J. Immunol.* 147:2964–2969), thus differentiating it from the protease of the present invention. Since proteolytically active ICE was isolated from the cytosol of monocytes and the monocyte line, THP.1 (Kostura, M. J., et al. (1989) *Proc. Natl. Acad. Sci.* 86:5227–52.31), it appears that synthesis of this protease is not sufficient to induce apoptosis in any cell line.

Other studies using protease inhibitors have implicated a role for proteolysis in apoptosis. For example, it has been suggested that TPCK inhibits chemotherapeutic drug-induced apoptosis in HL-60 cells (Bruno, S., et al. (1992) *Leukemia* 6, 1113–1120).

The effects of protease inhibitors have implicated the involvement of a serine protease in TNF-mediated tumor cell lysis (Suffys, P., et al. (1988) *Eur. J. Biochem.* 178, 251–256; Ruggiero, V., et al. (1987) *Cell. Immunol.* 107, 317–325), although these studies did not differentiate between TNF-induced necrosis or apoptosis.

Evidence from a recent study of the effect of a variety of protease inhibitors on T lymphocyte apoptosis induced by antibodies against the T cell receptor suggested two proteases may be involved (Sarin, A., et al. (1993) *J. Exp. Med.* 178, 1693–1700). One was postulated to be calpain or some other cysteine protease, whereas the other appeared to be a serine protease inhibited by DFP or PMSF. Although the U937 response was not inhibited by DFP or PMSF, it is not conclusive that the two serine proteases are different since the previous study did not isolate and characterize the T lymphocyte enzyme (Sarin, A., et al., supra). Taken altogether, these findings raise the possibility that apoptosis signal transduction may involve a proteolytic cascade. Indeed, we have unpublished evidence for activation of multiple proteases that cleave substrates different from the elastase-like substrate preferred by the 24 kDa protease from apoptotic U937 cells.

Recent progress in several laboratories studying the mechanism of cell-mediated cytotoxicity (CMC) has led to the discovery of several proteases that may be involved in apoptosis. According to the granule-exocytosis model of CMC (as reviewed in Bleackley, R. C., et al. (1988) *Immunol. Rev.* 10, 5–19 and Jenne, D., et al. (1988) *Curr. Top. Microbiol. Immunol.* 140, 33–47), after recognition of the target cell, the effector cell (cytoxic T lymphocyte (CTL) or NK cell) releases cytoplasmic granules that contain lytic mediators including cytolysin and a family of serine proteases (granzymes). Cytolysin is a pore-forming molecule that may act to promote the entry of the proteases into the target cell. Recent studies have shown that in the presence of cytolysin, or using detergent-permeabilized target cells, purified granzyme A/fragmentin 1 and fragmentins 2 and 3 can activate DNA fragmentation (Hayes, M. P., et al. (1989) *J. Exp. Med.* 170, 933–946; Shi, L., et al. (1992) *J. Exp. Med.* 176, 1521–1529; and Shi, L., et al. (1992) *J. Exp. Med.* 175, 553–556). However, the characteristics of these enzymes, summarized in Table 6, indicate they are clearly distinct from the protease of the present invention. Granzyme B and fragmentin 2 cleave tripeptide thiobenzyl ester substrates after aspartic acid. The protease of the invention is not closely related to human granzyme B since the latter is inactive on methoxysuccinyl-ala-ala-pro-val-thiobenzyl ester (SEQ ID NO: 4), a substrate preferred by elastase-like enzymes, Poe, M. P., et al. (1991) *J. Biol. Chem.* 266: 98–103. 1:enzyme A/fragmentin 1 and fragmentin 3 are tryptases that cleave the BLT substrate. However, the U937 protease is inactive on the BLT substrate while mediating high activity on a synthetic substrate preferred by elastase-like enzymes. U937 cells are known to contain high levels of leukocyte elastase that can be isolated in two MW forms of 30 and 60 kDa, Senior, R. M., et al. (1982) *J. Clin. Invest.* 69: 384–393. In addition to the molecular weight differences, the fact that commercially available leukocyte elastase cannot induce DNA fragmentation in U937 nuclei (FIG. 6A) indicates the protease of the present invention is not identical to leukocyte elastase. Thus, as summarized in Table 6, the 24 kDa U937 protease is distinct from proteases implicated as inducers of DNA fragmentation.

TABLE 6

The U937 Protease Differs from Leukocyte Elastase and Other Proteases Implicated as Inducers of DNA Fragmentation

| Protease | Source | MW | Substrate | Homolog | Ref. |
| --- | --- | --- | --- | --- | --- |
| Granzyme A/ Hanakah factor | Human CTL | 30 kDa reduced 60 kDa non-reduced | BLT | Fragmentin 1 | Hayes, M. P., et al. (1989) J. Exp. Med. 170, 933–946 |
| CC P1/Granzyme B | Murine CTL | 35 kDa reduced | Asp—ase | Fragmentin 2 | Lobe, C. G., et al. (1986) Proc. Natl. Acad. Sci. 83, 1448–1453 |
| Fragmentin 1 | Rat NK Cell | 30 kDa reduced | BLT | Granzyme A | Shi, L., et al. (1992) J. Exp. Med. 176, 1521–1529 |
| Fragmentin 2 | Rat NK Cell | 31 kDa non-reduced | Asp-ase | CCP1/ Granzyme B | Shi, L., et al. (1992) J. Exp. Med. 175, 553–556 |
| Fragmentin 3 | Rat NK Cell | 27 kDa non-reduced | BLT | Granzyme 3 | Shi, L., et al. (1992) J. Exp. Med. 176, 1521–1529 |
| 24 kDa Protease | Human U937 Cells | 24 kDa reduced or non-reduced | ala—ala—pro—val | | |
| Leukocyte Elastase | Human U937 Cells | 30 kDa reduced 60 kDa reduced | ala—ala—pro—val | | Poe, M. P., et al. (1991) J. Biol. Chem. 266, 98–103 |

TABLE 6-continued

The U937 Protease Differs from Leukocyte Elastase and Other Proteases Implicated as Inducers of DNA Fragmentation

| Protease | Source | MW | Substrate | Homolog | Ref. |
|---|---|---|---|---|---|
| ICE | Monocytes | 10 and 20 kDa subunits | IL-1β at Asp$^{116}$ Ala$^{117}$ | None | Thornberry, N. A., et al. (1992) Nature 356:768–774 and Howard, A. D., et al. (1991) J. Immunol. 147:2964–2969 |

The present invention provides substantially full length polypeptides having the 24 kDa protease activity described herein. In addition, the present invention provides for biologically active fragments of the polypeptides, or analogs or homologs thereof, including organic molecules which simulate the interactions of the peptides. Significant biological activities include protease activity, DNA fragmentation activity, and ligand binding activity. As used herein, "ligand" means a molecule that is recognized by a particular protease. The agent bound by or reacting with the protease is called a "ligand", a term which is definitionally meaningful only in terms of its counterpart protease. The term "ligand" does not imply any particular molecular size or other structural or compositional feature other than that the substance in question is capable of binding or otherwise interacting with the protease. Also, a "ligand" may serve either as the natural ligand to which the protease binds or interacts, or as a functional analogue that may act as an agonist or antagonist. Thus, the present invention provides methods for the affinity purification of ligands that interact with the protease. Ligands that can be investigated by this invention include but are not restricted to, agonists and antagonists for proteases, toxins and venoms, viral epitopes, hormones, sugars, cofactors, peptides, enzyme substrates, cofactors, drugs, and proteins.

Inhibitors of the 24 kDa proteaseb can be identified using protease assays well known in the art:, including any of the techniques described herein to detect proteolytic activity, especially using synthetic substrates (see, for example, Weaver et al., *Biochem Cell Biol* 71:488–500 (1993)). Typically a library of candidate inhibitors is screened in such assays. Candidate inhibitors can also be screened for the ability to inhibit UV-, anti-Fas antibody-, and TNF-induced apoptosis using the whole cell assays described herein for trypan blue exclusion or $^{51}$Cr release. Candidate inhibitors can also be screened for the ability to inhibit DNA fragmentation induced by the protease by the methods described herein, in addition to methods known in the art (see, for example, WO 93/112463).

Furthermore, peptide and protein inhibitors can be obtained by "panning" peptide or protein libraries displayed on filamentous bacteriophage against immobilized protease protein (For examples of techniques, see Roberts et al. (1992) *Gene* 121: 9–15; Dennis et al. (1995) *J Biol Chem* 270: 25411–25417; Wang et al. (1995) *J Biol Chem* 270: 12250–12256). Briefly, bound phage are eluted at low pH and amplified in host cells from which the protease-binding peptide sequences can be recovered by PCR. The protease-bindling peptides can then be tested for their ability to inhibit. protease activity.

Furthermore, nucleic acid encoding the protease can be used in cell-based screens for inhibitors. Such screens include the streptomycin-based screen of Balint and Plooy ((1995) *Nature Biotechnology* 13: 507–510) and the tetracycline-based screen of Block and Grafstrom ( (1990) *Antimicrob Agents Chemother* 34: 2337–41). Briefly, in the former, the protease is expressed in streptomycin-resistant *E. coli* cells along with a peptide substrate of the protease fused to wildtype ribosomal protein S12. The fusion protein is inactive until cleaved by the protease, whereupon active wildtype S12 is released, conferring protease-dependent streptomycin sensitivity on the cells. Either chemical or genetically-encoded libraries may then be screened with such cells for inhibitors of the protease by scoring for streptomycin resistance. In the tetracycline-based screen, a protease substrate peptide is encoded on the surface of the protein which confers tetracycline resistance on *E. coli*, such that when co-expressed in *E. coli* with the protease, protease-dependent tetracycline sensitivity is conferred by specific cleavage of the substrate. As with the streptomycin system, libraries may be screened for inhibitors of the protease by scoring for tetracycline resistance.

Transfected cells may be used as a model for studying apoptosis. For controlled investigation, mammalian cells lacking the 24 kDa protease may be transfected with an expression construct encoding the 24 kDa protease of the invention. Cells are produced that encode the protease that is often functionally equivalent to the wild-type protease. Thus, the binding properties of protease ligands may be analyzed, including naturally occurring and synthetic ligands. The transfected cells find particular use for the identification of ligands having pharmaceutical efficacy. Transfected cells may be contacted with a putative drug agent, and the amount of apoptosis modulation determined, as compared to the control cells in the absence of the putative drug. Ligands identified according to the invention find a variety of uses, including modulators of apoptosis, inhibitors of neurodegenerative diseases, tumors, viral diseases, and identification of tumor promoters.

The present invention also provides for other polypeptides comprising fragments of the protease of the invention and polypeptides substantially homologous thereto. The protease peptides of the invention will generally exhibit at least about 80% homology with naturally occurring sequences of the 24 kDa protease, typically at least about 85% homology, and more usually at least about 97% homology. The length of comparison sequences will generally be at least about 16 amino acid residues, usually at least about 20 residues, more usually at least about 24 residues, typically at least about 28 residues, and preferably more than about 35 residues.

The present invention also includes fusion polypeptides between the 24 kDa protease and other proteins. For example, homologous polypeptides may be fusions with other proteases, or other apoptosis-modulating proteins, resulting in fusion proteins having mixed functionalities. Similarly, fusions may be generated with heterologous proteins, for example a reporter polypeptide, e.g. bacterial beta-galactosidase, trpE, protein A, beta-lactamase, alpha amylase, alcohol dehydrogenase, and yeast alpha mating factor.

Such polypeptides may also have amino acid residues which have been chemically modified by phosphorylation, sulfonation, biotinylation, or the addition of other moieties. In some embodiments, the modification will be useful labeling reagents, or serve as purification targets, for example, affinity ligands.

Fusion polypeptides will typically be made by either recombinant nucleic acid methods or by synthetic polypeptide methods, as are generally described in Sambrook et al., supra; Merrifield (1963) *J. Amer. Chem. Soc.* 85: 2149–2156, Merrifield (1986) *Science* 232: 341–347, and Atherton et al. (1989) *Solid Phase Peptide Synthesis: A practical approach* IRL Press, Oxford.

The nucleic acid compositions of the invention will generally be in RNA or DNA forms, mixed polymeric forms, or any synthetic nucleotides structure capable of binding in a base-specific manner to a complementary strand of nucleic acid. An example of a suitable synthetic nucleotide structure is peptide nucleic acids, as described in Nielson, P. E., et al. *Science* (1991) 254:1497–1500. The described nucleic acid embodiment is typically derived from genomic DNA or cDNA, prepared by synthesis, or derived from combinations thereof. The DNA compositions generally include the complete coding region encoding the 24 kDa protease, or fragments thereof, e.g. comprising at least 8 codons, usually at least 12 codons, or usually at least about 15 codons, typically at least about 20 codons, more typically at least about 30 codons and preferably even more. One or more introns may be present.

The nucleic acids encoding the 24 kDa protease may be used to prepare an expression construct for the 24 kDa protease. The expression construct normally comprises one or more DNA sequences encoding the 24 kDa protease operably linked and under the transcriptional control of a native or other promoter. Usually the promoter will be a eukaryotic promoter for expression in a mammalian cell. The transcriptional regulatory sequences will typically include a heterologous promoter or enhancer which is recognized by the host cell. The selection of an appropriate promoter will depend on the host cell. Examples of suitable promoters include trp, lac, phage promoters, tRNA promoters, and glycolytic enzyme promoters. Convenient expression vectors are commercially available.

The expression construct will often be contained in a vector capable of stable extrachromosomal maintenance in an appropriate cellular host or may be integrated into the host genome. As used herein, "host" or "host cell" includes any suitable prokaryotic or eukaryotic cell. The expression construct may be bordered by sequences which allow for insertion into a host, such as regions of homology for homologous recombination, transposon sequences, lysogenic viral sequences, and the like. Normally, the expression construct additionally includes cis or trans markers, preferably cis markers, for selection of host cells containing the construct. In mammalian cells, the protease gene itself may provide a convenient marker. However, in prokaryotic host cells, markers such as resistance to a cytotoxic agent, complementation of an auxotrophic host to prototrophy, production of a detectable product, and the like, may be more convenient.

Polyclonal and/or monoclonal antibodies to the protease of the present invention may be prepared. The gene or synthetic peptide fragments thereof may be prepared as described herein, and coupled to a carrier molecule, for example keyhole limpet hemocyanin, and injected into rabbits at selected times over several months. The rabbit sera may be tested for immunoreactivity to the protease or fragments thereof. Monoclonal antibodies may be made by injecting mice with the protease or synthetic peptide fragments thereof. Monoclonal antibodies may be screened by methods known in the art, as are described, for example, in Harlow and Lane (1988) *Antibodies: A laboratory manual*, Cold Spring Harbor Press, New York, and Goding (1986) *Monoclonal antibodies: Principles and Practice* (2d ed.) Academic Press, New York. The antibodies will be tested for specific immunoreactivity with an epitope of the protease. These antibodies will find use in diagnostic assays or as an active ingredient in a pharmaceutical composition.

For production of polyclonal antibodies, an appropriate target immune system is selected, typically a mouse or rabbit, although other species such as goats, sheep, cows, guinea pigs, and rats may be used. The substantially purified antigen is presented to the immune system according to methods known in the art. The immunological response is typically assayed by an immunoassay. Suitable examples include ELISA, RIA, fluorescent assay, or the like. These antibodies will find use in diagnostic assays or as an active ingredient in a pharmaceutical composition.

The compositions of the present invention have utility for modulating the growth and differentiation of cells through the apoptotic process. Modulation of the apoptotic process includes deceleration of the rate of apoptosis in a population of cells, or elimination of the cellular apoptotic response to apoptosis inducing agents. Modulation of the apoptotic process also includes induction or acceleration of apoptosis where it is desirable to increase the rate of cell death or to specifically target a population of cells. For example, the induction of apoptosis in tumor cells or in other cells showing increased proliferation and growth provides an effective therapy to decrease or abolish the growth of these cells. The compounds of the present invention also have utility in combating drug resistance, which is a common problem with current cancer treatments. Drug resistance may be a resistance to apoptosis in general, and thus, the proteases of the present invention may be used to decrease drug resistance. In this embodiment, the compounds of the invention may be used in conjunction with other antineoplastic agents. Mechanisms of drug resistance are described, for example, in Remington's Pharmaceutical Sciences, 18th Edition, supra. In some embodiments, the compositions of the invention may be used to assay tissue injury and regeneration. A suitable model system for the assay of tissue injury is the thymus of dexamethasone treated rats, as described in Schwartzman, Robert et al. (1991) Endocrinology 128:2 1190–1197, the contents of which are hereby incorporated by reference.

The compositions of the present invention thus have utility for a variety of therapeutic indications, including as anti-viral, anti-microbial, or anti-parasitic agents, as neoplastic agents for the treatment of acute lymphoblastic or myeloid leukemia, chronic myeloid, myelogenous, granulocytic, or lymphatic leukemia, acquired immune deficiency syndrome (AIDS), neurogenerative diseases, myelodysplatic syndrome, Hodgkin's lymphoma, malignant lymphomas such as non-Hodgkin's lymphoma, or Burkitt's lymphoma, neoplasms and the like.

The quantities of active ingredient necessary for effective therapy will depend on many different factors, including means of administration, target site, physiological state of the patient, and other medicaments administered. Thus, treatment dosages should be titrated to optimize safety and efficacy. Typically, dosages used in vitro may provide useful guidance in the amounts useful for in situ administration of the active ingredients. Animal testing of effective doses for treatment of particular disorders will provide further predictive indication of human dosage. Various considerations are described, for example, in *Goodman and Gilman's the Pharmacological Basis of Therapeutics*, 7th Edition (1985), MacMillan Publishing Company, New York, and *Remington's Pharmaceutical Sciences* 18th Edition, (1990) Mack Publishing Co, Easton Penn. Methods for administration are discussed therein, including oral, intravenous, intraperitoneal, intramuscular, transdermal, nasal, iontophoretic administration, and the like.

The pharmaceutical compositions may be administered in a variety of unit dosage forms depending on the method of administration. For example, unit dosage forms suitable for oral administration include solid dosage forms such as powder, tablets, pills, capsules, and dragees, and liquid dosage forms, such as elixirs, syrups, and suspensions. The active ingredients may also be administered parenterally in sterile liquid dosage forms. Gelatin capsules contain the active ingredient and as inactive ingredients powdered carriers, such as glucose, lactose, sucrose, mannitol, starch, cellulose or cellulose derivatives, magnesium stearate, stearic acid, sodium saccharin, talcum, magnesium carbonate and the like. Examples of additional inactive ingredients that may be added to provide desirable color, taste, stability, buffering capacity, dispersion or other known desirable features are red iron oxide, silica gel, sodium lauryl sulfate, titanium dioxide, edible white ink and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

The invention will now be further described by references to the following experimental examples, which are intended to be exemplary, and not scope-limiting.

EXAMPLE 1

Cell Lines and Reagents

The human histiocytic lymphoma, 13937, the human mammary carcinoma BT-20, the human myelocytic leukemia HL-60, and the murine fibroblast cell line 3T3 were obtained from the ATCC (Rockville, Md.). All cell lines were maintained in antibiotic-free RPMI 1640 supplemented with 10% FCS and 1-glutamine (2 mM). All cell lines were routinely tested for mycoplasma and always found to be negative according to the Mycotect kit (GIBCO, Grand Island, N.Y.).

Purified human rTNF (specific activity=$1 \times 10^7$ U/mg) was purchased from R&D Systems, Minneapolis, Minn. DNase I was purchased from Worthington (Freehold, N.J.), micrococcal nuclease (116 U/mg) was from Calbiochem (San Diego, Calif.). All substrates for the protease assays and protease inhibitors (except DK120) were purchased from Sigma (St. Louis, Mo.). DK120 was prepared as described in Example 8. Trypsin and chymotrypsin were obtained from Sigma, and human leukocyte elastase was obtained from Calbiochem.

EXAMPLE 2

DNA Fragmentation Assay

DNA fragmentation assays were carried out according to the protocol of Wright S. C., et al. (1,992) *J. Cell. Biochem.* 48, 344–355. Target cells were labeled with $^3$H-thymidine and plated in triplicate in flat bottom microtiter plates. Cells were incubated for the indicated length of time for each experiment in the presence of TNF or various inhibitors. In some experiments, cells were treated with UV light at 245 nm using a UV Crosslinker (Fisher Scientific). Assays were harvested and counted on a Packard matrix 96 beta counter. Percent DNA fragmentation was calculated as for the nuclear assay described in Example 3. In assays to test the effects of various inhibitors, the pH of extra wells containing assay buffer, target cells, and each inhibitor was always checked at the beginning and end of each assay to assure that the pH remained at 7.5.

EXAMPLE 3

DNA Fragmentation Assay Using U937 Nuclei Targets

U937 cells were labeled with $^3$H-thymidine by culturing overnight with isotope at 0.5 $\mu$Ci/ml. The cells were pelleted, washed once, and the cytoplasmic membrane lysed by resuspending the cells in assay buffer (50 mM Tris, 250 mM sucrose 10 mM MgSO$_4$, pH 7.5) plus 0.02% NP-40. Nuclei were then pelleted and resuspended in assay buffer at $1 \times 10^6$/ml. The assay was set up in triplicate in flat bottom microtiter plates under sterile conditions. Nuclei (0.05 ml) were mixed with 0.05 ml of sample diluted in 50 mM Tris pH 7.5 or buffer alone to determine total counts. Plates were incubated for 5 h at 37° C. and then harvested by the addition of 0.1 ml of harvesting buffer (10 mM Tris, 10 mM EDTA, 0.3% Triton X-100, pH 7.5). Plates were harvested by filtration onto glass fiber paper and counted on a Packard Matrix 96 beta counter. Percent DNA fragmentation was calculated as follows:

total cpm−test cpm/total cpm×100

EXAMPLE 4

Visualization of DNA Fragmentation by Gel Electrophoresis

DNA fragmentation was carried out according to the procedure of Example 2. After the desired treatments, the cells were lysed and debris was removed by centrifugation at 13,000×g for 10 sec. DNA in the supernatant was ethanol precipitated after phenol extraction. Equivalent amounts of material from a fixed number of cells were loaded and electrophoresed on a 1.0% agarose slab gel. DNA was visualized by ethidium bromide staining.

EXAMPLE 5

Visualization of DNA Fragmentation by Gel Electrophoresis

DNA fragmentation was carried out according to the procedure of Examples 2 and 3. The assay was adapted to assess the effects of compounds on DNA fragmentation in isolated nuclei. Nuclei were prepared from normal unlabeled U937 cells as described in Example 3. After the desired treatments of aliquots of $5 \times 10^6$ nuclei, 1.0 ml of harvesting buffer (see Example 3) was added and debris was removed by centrifugation at 13,000×g for 10 sec. DNA in the supernatant was ethanol precipitated after phenol extraction. Equivalent amounts of material from a fixed number of cells were loaded and electrophoresed on a 1.0% agarose slab gel. DNA was visualized by ethidium bromide staining.

EXAMPLE 6

Nuclease Assay With U937 DNA as Substrate $^3$H-thymidine-labeled DNA was prepared by incubating U937 cells with isotope at 0.5 $\mu$Ci/ml for 24 h. The cells were washed and DNA was isolated according to the procedure of Sambrook, J., et al. (1989) *Molecular Cloning*, Cold Spring Harbor Laboratory Press, New York, vol. 2, p. 9.22. $^3$H-labeled U937 DNA was diluted to 75 μg/ml in 50 mM Tris, 10 mM MgSO$_4$, 1 mM CaCl$_2$, pH 7.5. 0.05 ml of substrate and 0.05 ml of sample were mixed in Eppendorf tubes and incubated at 37° C. for 20 h. The assay was terminated by the addition of 0.05 ml of 0.5% BSA plus 0.05 ml of 7% perchloric acid and placed on ice for 15 min. The intact DNA was pelleted by centrifugation at 13,000×g for 15 min and the radioactivity in 0.1 ml of the supernatant assessed by scintillation counting. The % DNA fragmentation was calculated as the measured cpm in the supernatant divided by the total cpm of the original DNA added×100.

EXAMPLE 7

Protease Assays

Proteolytic activity was assayed using synthetic substrates selective for different known proteases. All assays were set up by adding 0.02 ml of sample (or known enzyme as a positive control) plus 0.18 ml of appropriate substrate dissolved in PBS PH 7.5 in triplicate in flat bottom microtiter plates, incubated for the indicated length of time at room temperature, and the OD at 405 nm measured using a plate reader.

To measure chymotrypsin-like activity, N-succinyl-ala-ala-pro-phe p-nitroanilide (SEQ ID NO: 2) (SAAPP) at 0.1 mM was used as the substrate. Trypsin-like activity was measured using N-α-benzyloxycarbonyl-L-lysine thiobenzyl ester (BLT) at 0.2 mM plus 0.11 mM nitrobenzoic acid.

Elastase-like activity was measured using N-methoxysuccinyl-ala-ala-pro-val p-nitroanilide (SEQ ID NO: 3) (MAAPV) at 0.25 mM as a substrate. For convenience and maximum sensitivity, these assays were routinely incubated 20 h to monitor protease purification. Under these conditions, the elastase dose response was linear up to a concentration of 6.0 μg/ml (OD of 1.0), see FIG. 3C. The activity of the protease samples tested during purification did not exceed an OD of 1.0 under these assay conditions. In order to quantitate the activity of the purified protease, identical assays were set up but kinetic readings of OD were taken every hour from 1–6 h. One unit of enzyme was calculated as the amount of enzyme that hydrolyzes 1.0 nmol substrate/h.

EXAMPLE 8

Preparation of the DK120 Affinity Resin

The synthesis and characterization of the boronic acid amino acid analog protease inhibitor (DK120) as well as the non-inhibitory boronic acid compound, IBA, was as described in Kinder, D. H., et al. (1985) *J. Med. Chem.* 28 1917–1925, and Kinder, D. H., et al. (1991) *Invasion and Metastasis* 12 309–319. DK120 is a tripeptide reversible inhibitor of chymotrypsin (carbobenzoxy-ala-ala-borophe) in which a boronic acid is in place of COOH at the site of enzymatic serine OH attack. Affinity resin was prepared in a manner similar to that described in Emod, et al. (1978) *Affinity Chromatography ed.* Hoffman-Ostenkof, O. et al. Pergamon Press, UK pp. 123–128, and Billings, P. C., et al., (1988) *Cancer Res.* 48, 1798–1802, except that epoxy activated Sepharose 6B was used instead of cyanogen bromide activated resin, Sundberg, L., et al. (1974) *J. Chromatogr.* 90, 87–98. DK120 was N-de-blocked by hydrogenation in the presence of 5% Pd/carbon (10l weight) in 9.5% ethanol. Catalyst was removed by filtration through celite, and the ethanol was evaporated. The resulting oily residue was dried under vacuum for at least 1 h to remove excess alcohol. The de-protected product was dissolved in dimethylformamide (DMF) for coupling to the resin. Sepharose 6B (Sigma) was swollen with water, then reacted with DK120 at pH 10 in 0.1 M NaOH/DMF (1:1) for 16–24 h at 37° C. The resin was subsequently washed with DMF, followed by water. The derivatized resin was then treated with 1 M ethanolamine at room temperature for 4 h. The resin was then rinsed sequentially with water, acetate buffer, pH 4.0, and finally with borate buffer, pH 8.0. The affinity resin was stored in 20% ethanol prior to use. A control resin was prepared that lacked the DK120 ligand but was treated with ethanolamine and washed as described above.

EXAMPLE 9

Preparation of Cell Lysates for Protease Purification

Normal or UV light-treated (0.2 J/cm$^2$ in a UV Crosslinker) cells were pelleted and resuspended at 2×10$^8$/ml in ice cold lysing buffer (50 mM Tris, 0.3% NP-40, pH 7.0). The debris was pelleted by centrifugation in a microfuge at 14,000×g for 15 min. The supernatant was used immediately or stored at −70° C. until further purification.

EXAMPLE 10

DK120 Affinity Chromatography

One ml of affinity resin was equilibrated with starting buffer (50 mM Tris pH 7.5, 100 mM NaCl, 1.0 mM CaCl$_2$, 0.1% NaN$_3$, and 0.05% Tween 20). Cell lysate was mixed with the resin and allowed to bind for 60 min. The column was then washed with starting buffer at 0.5 ml/min until the OD$_{280}$ returned to baseline. Bound material was eluted with starting buffer plus 0.1% HCl pH 4.5. During elution, 1.0 ml fractions were collected and immediately neutralized to pH 7.5. The column was regenerated by washing with 2.0 M NaCl (no additional protease was eluted during this step).

EXAMPLE 11

Heparin Sepharose Affinity Chromatography

Heparin Sepharose (Pharmacia) was equilibrated in starting buffer (50 mM Tris pH 7.5, 1.0 mM CaCl$_2$, 0.05% Tween 20, 0.1% NaN$_3$). Active fractions eluted from the DK120 column were applied followed by washing with starting buffer at 0.5 ml/min until the OD$_{280}$ returned to baseline. Bound material was eluted with a linear gradient from 0 to 2.5 M NaCl in starting buffer. One ml fractions were collected and tested for protease activity. All flow-through fractions were negative for protease activity whereas proteases showing activity against the MAAPV substrate eluted at 1.0–1.5 M NaCl.

EXAMPLE 12

Reverse Phase (RP) HPLC

Separations were performed on a Waters 625 liquid chromatography system using a 3 cm×2.1 mm C4 cartridge (Brownlee). Buffer A was water plus 0.1% trifluoroacetic acid and buffer B was 80% 2-propanol plus 0.1% trifluoroacetic acid. Bound material was eluted using a linear gradient from 75%A/25%B to 35%A/65%B over 60 min at a flow rate of 0.2 ml/min. 0.2 ml fractions were collected and immediately neutralized to pH 7.5. All fractions were tested for protease activity as well as nuclear DNA fragmenting activity.

EXAMPLE 13

SDS PAGE

Protease purity was assessed using 15% Laemmi SDS gel electrophoresis followed by silver staining using the Daiichi II kit (ISS, Hyde Park, Mass.). Protezase was purified from UV light-treated U937 cells and the active fraction #41 from the RP separation shown in FIG. 7 was analyzed by SDS PAGE under non-reducing conditions, revealing a 24 kDa band. Identical results were observed under reducing conditions.

EXAMPLE 14

DK120 Attenuates TNF but not Anti-Fas-Induced Hepatotoxicity in Vivo

In this example the concept that a protease inhibitor such as DK120 may attenuate inappropriate apoptosis that causes tissue damage in systemic inflammatory response syndrome (SIRS) was tested. TNF-induced hepatocyte apoptosis in mice was performed as described by Leist et al. ((1995) *J. Immunol.* 154:1778–1786). Briefly, Balb/c mice were injected ip with 45 mg murine TNF combined with 15 mg Actinomycin D/mouse. Twelve h later, mice were anesthetized and bled from the heart to measure serum transaminase levels, which are standard clinically used indicators of liver damage. Mice that were treated with protease inhibitors were injected ip with these compounds 30 min. prior to TNF. Alanine aminotransferase (ALT) and aspartate aminotransferase (AST) were assayed using a commercially available kit (Sigma). The results in Table 7 demonstrate that injection with TNF caused a 5.7 fold increase in ALT and a 1.6 fold increase in AST compared to serum from mice injected with Actinomycin D alone. However, treatment with DK120 caused a doss-dependent decrease in serum transaminase levels. The optimal dose of 10 mg/kg of DK120 reduced transaminase to levels very close to those seen in mice injected with Actinomycin D only. These findings suggest that DK120 attenuates hepatocyte apoptosis induced by TNF. However, a drug that nonspecifically blocks all apoptotic pathways that normally function to maintain homeostasis may not be clinically desirable. Subsequent studies were performed to determine if DK120 could also suppress hepatocyte apoptosis in response to a different stimulus.

TABLE 7

DK120 Attenuates TNF-Induced Hepatotoxicity

| Treatment[1] | ALT (U/ml) | AST (U/ml) |
| --- | --- | --- |
| None | 39 | 51 |
| Actinomycin D 15 mg | 70 | 47 |
| "+ TNF 45 mg | 398 | 78 |
| "+ "+ DK120 10 mg/kg | 50 | 56 |
| "+ "+ DK120 5 mg/kg | 123 | ND |
| "+ "+ DK120 2.5 mg/kg | 145 | 47 |
| "+ "+ DK120 1 mg/kg | 232 | 64 |

[1]Mice (2 for each treatment) were injected ip +/- DK120 30 min prior to TNF and Actinomycin D. Twelve h later serum transaminase levels were measured.

It has been previously shown that injection of mice with antibodies directed against the Fas antigen causes hepatocyte apoptosis and death due to liver failure (Ogasawara et al. (1993) *Nature* 364:806–809). Therefore, the effects of administration of DK120 to mice injected with antibodies directed against the murine Fas antigen were tested. The results shown in Table 8 demonstrate that treatment with DK120 did not counteract the elevation of serum transaminases induced by anti-Fas antibodies. Therefore, this protease inhibitor does not nonspecifically block all apoptotic pathways. This result is in accord with other reports that TNF and anti-Fas activate different apoptotic pathways (Wong et al. (1994) *J. Immunol.* 152:1751–1755). This may be clinically important since evidence indicates that Fas-Fas ligand interactions are important in maintaining homeostasis in lymphoid immune responses (Nagaki et al. (1995) *Gastroenterology* 106:450–458).

TABLE 8

DK120 Does Not Inhibit Anti-Fas Induced Hepatotoxicity

| Treatment[1] (U/ml) | ALT (U/ml) | AST |
| --- | --- | --- |
| None | 35 | 41 |
| anti-Fas 2 mg | 513 | 81 |
| "+ DK120 5 mg/kg | 746 | 121 |

[1]Mice (2 for each treatment) were injected ip +/- DK120 30 min prior to anti-Fas antibodies. Twelve h later serum transaminase levels were measured.

EXAMPLE 15

Figure 9:
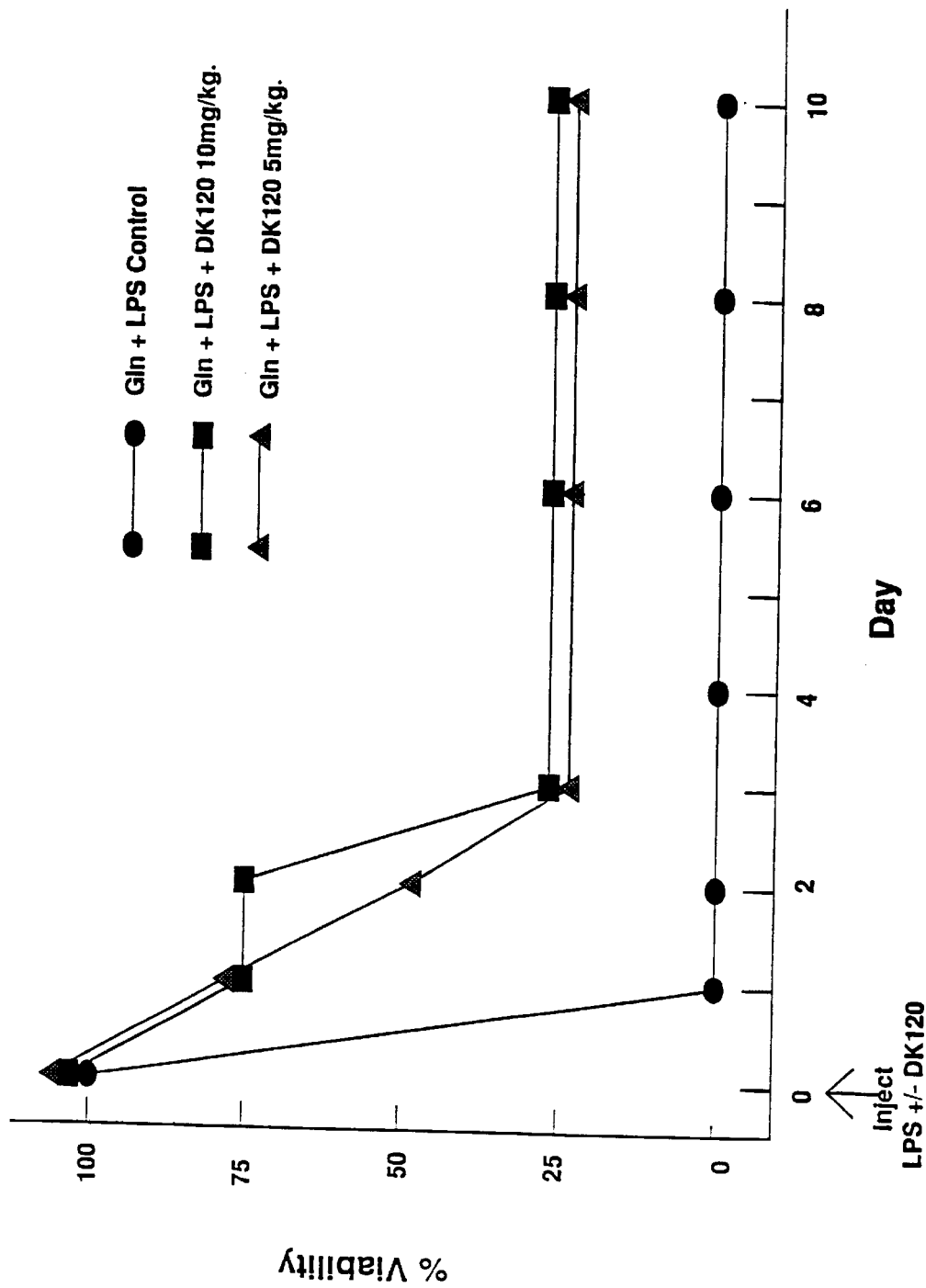
FIG. 9 depicts the ability of DK120 to delay or prevent LPS-induced mortality.

DK120 Attenuates Hepatotoxicity and Decreases Mortality in LPS and SEB Models of SIRS In this example experiments were performed to determine if treatment with DK120 could attenuate the deleterious effects of endogenous TNF induced by injection of bacterial toxins. Mice were sensitized to the lethal effects of lipopolysaccharide (LPS) or Staphylococcccal enterotoxin B (SEB) by co-injection with galactosamine (Gln). The results in Table 9 show that injection of DK120 30 min prior to the toxins caused a significant reduction in the serum transaminase levels. Furthermore, none of the treated animals died, although 1 out of 3 of the untreated LPS or SEB injected animals died. But since this experiment was terminated at 20 h by sacrificing all survivors, long term mortality could not be determined. Therefore, in the next experiment, mice were treated +/- DK120, injected with LPS plus Gln, and scored for long term survival. The results shown in FIG. 9 demonstrate that DK120 could delay or prevent LPS-induced mortality.

Without being limited to any one theory, the fact that DK120 alone is a relatively toxic compound probably accounts for the inability of DK120 treatment to prevent mortality in 100% of the mice. In preliminary studies daily injection of mice with DK120 at 20 mg/kg was lethal. The reason for toxicity is not clear but may be related to the ability of DK120 to inhibit chymotrypsin-like enzymes that may be essential for the normal function of various tissues.

TABLE 9

DK120 Attenuates LPS and SEB-Induced Hepatotoxicity

| Treatment[1] | % Mortality | ALT (U/ml) | AST (U/ml) |
| --- | --- | --- | --- |
| Gln 15 mg | 0 | 137 +/- 33 | 67 +/- 4.6 |
| Gln + LPS 0.05 mg | 33 | 334 | 100 |
| Gln + LPS + DK120 5 mg/kg | 0 | 182 +/- 17 | 79 +/- 10 |
| Gln + SEB 5 mg | 33 | 339 | 119 |

TABLE 9-continued

DK120 Attenuates LPS and SEB-Induced Hepatotoxicity

| Treatment[1] | % Mortality | ALT (U/ml) | AST (U/ml) |
|---|---|---|---|
| Gln + SEB + DK120 5 mg/kg | 0 | 205 +/− 28 | 72 +/− 13 |

[1]Mice (3 for each treatment) were injected ip +/− DK120 30 min prior to galactosamine (Gln) and LPS. Twelve h later serum transaminase levels were measured in those mice that survived.

EXAMPLE 16

Specificity of DK120 Attenuation of TNF-induced Hepatotoxicity

To further explore the specificity of DK120 attenuation of TNF-induced hepatotoxicity, several compounds were tested that were found previously not to inhibit apoptotic protease proteolytic activity as measured against a synthetic substrate (data not shown). Isobutyl boronic acid (IBA)is a boron-containing compound that has no protease inhibitory activity. The results shown in Table 10 demonstrate that IBA does not protect from TNF-induced hepatotoxicity in mice. Therefore, the protection mediated by DK120 is not a property of any boron-containing molecule.

Aprotinin, a broad-spectrum protease inhibitor, and eglin, an elastase inhibitor were also tested. These compounds were chosen since they do not inhibit apoptotic protease and also because they had been tested for inhibition of tissue damage or coagulation in animal models of SIRS (Cumming et al. (1992) Crit. Care Med. 20:1134–1139; Siebect et al. (1989) Prog. Clin. Biol. Res. 308:945–951). As shown in Table 10, neither of these inhibitors had much effect on ALT levels as compared to DK120 which reduced levels of ALT to close to that of Actinomycin D alone. Thus, the capacity to prevent TNF-induced hepatotoxicity is not a property of any protease. These findings indicate that inhibition of the apoptotic protease of the invention by DK120 counteracts TNF-induced liver cell apoptosis.

TABLE 10

Specificity of DK120 Protection From TNF-Induced Hepatotoxicity

| Treatment[1] | ALT (U/ml) |
|---|---|
| Exp. #1 | |
| Actinomycin D 15 mg | 71 +/− 8.5 |
| Actinomycin D 15 mg + TNF 45 mg | 425 +/− 64 |
| Actinomycin D 15 mg + TNF 45 mg + DK120 10 mg/kg | 190 +/− 21 |
| Actinomycin D 15 mg + TNF 45 mg + IBA 10 mg/kg | 393 +/− 52 |
| Actinomycin D 15 mg + TNF 45 mg + Aprotinin 10 mg/kg | 346 +/− 14 |
| Exp. #2 | |
| Actinomycin D 15 mg | 139 +/− 29 |
| Actinomycin D 15 mg + TNF 45 mg | 465 +/− 12 |
| Actinomycin D 15 mg + TNF 45 mg + DK120 10 mg/kg | 141 +/− 20 |
| Actinomycin D 15 mg + TNF 45 mg + Eglin 10 mg/kg | 316 +/− 11 |

[1]Mice (3 for each treatment) were injected ip +/− the inhibitors 30 min prior to TNF and Actinomycin D. Twelve h later serum transaminase levels were measured.

EXAMPLE 17

Inhibitors of the Protease

A. Design of Libraries

Combinatorial chemical libraries are a new approach to screen large numbers of novel compounds for the desired pharmaceutical application (for review see Ecker et al. (1995) Biotechnology 13:351–360; Janda (1994) Proc Natl Acad Sci 91:10779–10785). This technology has been successfully used to identify novel inhibitors of trypsin (Eichler et al. (1993) Biochem 32:11035–11041) and the HIV protease (Owens, et al. (1991) Biochem Biophys Res Commun 181:402–4108). In this example, the search for an apoptotic inhibitor employs a recursive deconvolution strategy (Erb et al. (1994) Proc Natl Acad Sci 91:11422–11426) to analyze the active member(s) of a synthetic peptide library.

Serine proteases contain a catalytic triad in their active sites composed of a serine hydrosyl, histidine residue, and an aspartate residue for enhancing the nucleophilicity of the serine hydroxyl group for attack on the scissile peptide bond. Inhibitors of serine proteases must either interact with the serine hydroxyl in such a manner that it enhances binding, or avoid spacial conflicts with the catalytic triad. This example focuses on libraries containing peptides which are known to inhibit proteases, i.e., compounds with a reduced amide bond (amino methyl) in place of the usual amide bond[1]. This substitution was originally introduced to prevent hydrolysis of the peptide analog at the scissile amide bond, and has the additional property of inhibiting the hydrolytic enzymes as well. This type of compound is readily prepared by reductive alkylation of the Schiff's base formed from the free a-amino group of the nascent peptide with a protected a-amino aldehyde. The amino aldehydes are commercially available, and the reductions can be carried out using solid phase methodology (Sasaki et al. (1987) Peptides 8:119–121).

Six pentapeptide libraries will be prepared, each containing one defined residue. These are of the form: $Ac-X_1-X_2-D_3-X_4-X_5$ (SEQ ID NO: 5), where $D_3$ is one (of 6 possible) defined residue on the amino terminus side of the scissile peptide bond. The bond will be reduced on the carboxy terminus of this amino acid. X represents one of the 15 randomized amino acids of the alphabet as described below.

Since the apoptotic protease is known to bind substrates with P1 aliphatic and aromatic side chains, aldehyde amino acids phenylalaninal, valinal, leucinal, isoleucinal, alaninal, and tyrosinal will be used to produce the initial 6 libraries. All aldehydes are available commercially, although any of these aldehycies can also be synthesized by techniques commonly used in the art.

Libraries are deconvoluted as described recently by Erb et al. ((1994) Proc Natl Acad Sci 91:11422–11426) in which a portion of the mixed resin is saved at each cycle of addition of the monomers. Thus, the active sequence can be readily identified with minimal re-synthesis of peptides.

The apoptotic protease has demonstrated a preference for P1 aromatic and aliphatic amino acids which has dictated the choice of aldehyde to produce the reduced bond at position D as indicated above. The remaining letters of the alphabet for the X positions consist of 15 normal L-amino acids. They exclude arginine, histidine, tryptophan, lysine, and cysteine.

Briefly, the reduced peptide bond isostere is prepared from the amino acid aldehyde and a second amino acid by first forming a Schiff's base in dimethylformamide (DMF) followed by reduction with $NaBH_3CN$. This step is repeated to ensure complete coupling of the aldehyde to the nascent peptide. In the combinatorial format, the usual coupling will be carried out for the 15 letters of our the alphabet for the first two positions, $X_1$ and $X_2$. After each coupling, a portion of the resin (constituting the p(1) and p(2) libraries, and so forth for each cycle) is catalogued and set aside for use during deconvolution. After the second cycle, the resins are combined, mixed and redistributed into 6 equal portions for addition of one of each of the 6 aldehyde amino acids. The remaining two amino acid positions are randomized as usual. Following the synthesis, the N-terminal amino acid(s) are capped with acetic anydride/pyridine.

The peptides are synthesized on Wang type resins using Fmoc-protected amino acids. Briefly, sufficient resin is weighed out to produce 250 mg of peptides following cleavage from the resin. A 10% loss of nascent peptide per cycle is assumed for the sake of calculations. Equal amounts of resin (Bachem) with the 15 amino acid alphabet are combined. The protecting group is removed with 30% diethylamine in methylene chloride (0.5 hr), followed by rinsing until diethyl amine is removed. The composite resin is divided into 15 equal portions, and one of the 15 letters is coupled to each portion using the following protocol. Protected amino acid, 2 equivalents (eq.), is added to the resin which has been swollen with dimethyl formamide or methylene chloride. This is followed by 2 eq. of 1-(3-dimethylaminopropyl)-3-ethylcarbodiimide hydrochloride (DMF) containing 2 eq. HOBT as racemization suppressing agent, and then by 2 eq. triethylamine in methylene chloride. The samples are shaken for 2–3 h, solvents are removed and rinsed with methylene chloride, and the cycle is repeated. Following the second cycle, resin is checked with ninhydrin (except for proline) to assure complete coupling has occurred. The samples are combined, deprotected with diethylamine, dried, and redistributed for the addition of the second letters. The 6 aldehydes are coupled to the resin following the addition of the second letter, and the last 2 letters of the library are added as described above.

Initially 6 different libraries are tested, each containing a different known residue at $D_3$ and a mixture of 15 different amino acids at all X positions. The library that exhibits the most inhibitory activity (presumably dictated by the defined $D_3$ residue), is analyzed for the correct amino acid at position $X_5$. This is done by retrieving the aliquot of the p(4) library that served as the precursor of the library selected from the final 6 libraries. This p(4) library is then divided into 15 equal aliquots, and one of each of the 15 letters of the alphabet is coupled to the peptides. The resulting pentapeptides are then screened L:o determine which of the 15 mixtures exhibits the most inhibitory activity. In this way, the most active amino acid at position $X_5$ is revealed. The next step is to retrieve the sample of the p(3) library, divide into 15 aliquots, and couple one of each of the 15 letters to produce 15 p(4) libraries, each containing a known amino acid at position $X_4$. The most active amino acid selected previously for position $X_5$ is then coupled to all the mixtures and the resulting libraries tested in the screening assays to determine the correct amino acid for position $X_4$. The same process is repeated using the amino acids selected for $X_5$ and $X_4$ to determine the best amino acids for positions $X_2$ and $X_1$. Since the residue at position $D_3$ is known from the start, this process will define the entire pentapeptide that inhibits the screening assays.

It is possible that more than one of the initial 6 libraries tested is inhibitory. In that event, the most potent inhibitor is determined by titrating out the libraries in the screening assays. If 2 or more libraries exhibit equal potency, both libraries can be deconvoluted, since the microtiter format screening assays can easily accommodate large numbers of samples. For example, in the very unlikely event that all 6 of the initial libraries show potent inhibition, the next deconvolution step would produce only 6×15=90 samples to test.

An issue that is taken into consideration in the design of combinatorial libraries is whether the initial libraries tested will contain a sufficiently high concentration of the active species to be detected in the screening assays. The expected recovery is approximately 200 mg of peptides for each of the 6 initial libraries. If the average MW of each peptide is 550, then each library should contain 364 mmol total of all peptides. The complexity at each X position is 15, whereas the complexity at the known $D_3$ position is 1. Thus, the overall complexity is 15×15×1×15×15=50,625. Therefore, there should be a total of 364 mmol÷50,625=7.19 nmol total of each species of peptide. The maximum amount anticipated for the initial screen is 5% of the total material/microtiter well. Testing this amount of peptide in 4 screening assays in triplicate will consume 60% of the original library, which will leave sufficient material to repeat testing at decreasing concentrations. The maximum amount tested will yield a final concentration of each peptide species in the assay of 1.8 mM (based on a 1:10 dilution when 5% of the library is added to the assay). This concentration is much higher than what would be expected for the $IC_{50}$ of a good protease inhibitor. Indeed, the design of these libraries should yield protease inhibitors with $IC_5$. values in the range of 10–100 nM, based on the synthesis of renin inhibitors which have the same isostere substituted for the scissile amide bond (Blundell et al. (1987)*Biochemistry* 26:5585–5590).

At each step of the deconvolution, the concentration of the active species should increase in proportion to the alphabet size, i.e. 15 fold. If an increase in the potency of inhibition is not observed, a false positive is suggested. The initial libraries would then be retested.

The potency of the best drug candidate can be increased by building a library based on this structure to extend the amino acid pattern beyond 5 in the manner recently described by Ostresh et al. ((1994) *Proc Natl Acad Sci* 91:11138–11142). In this method the most active peptides are used as the base for adding additional randomized amino acids to enhance activity.

B. Screening of Libraries

Libraries are screened using a sequential series of assays starting with the simplest and least specific and progressing to the most biologically relevant in vitro assays. For example, libraries are initially screened for inhibition of apoptotic protease activity against a synthetic chromogenic substrate. This assay is simple, rapid (can be completed in one day) and in microtiter format, thus facilitating testing of large numbers of samples. This assay detects any compounds that inhibit apoptotic protease activity. Positive samples are subsequently tested in a nuclear assay. Exemplary methods are provided below.

1. Affinity Purification of Apoptotic Protease

Apoptotic protease is purified from U937 cells undergoing apoptosis in response to UV light as described in detail above. Briefly, UV light-treated (0.2 J/cm$^2$ in a UV Crosslinker) cells are pelleted and resuspended at 2×10$^8$/ml in ice cold lysing buffer (50 mM Tris, 0.3% NP-40, pH 7.0). The debris is pelleted by centrifugation in a microfuge at 14,000×g for 15 min. The supernatant is purified on the DK120 affinity column immediately or stored at −70° C.

The synthesis and characterization of the boronic acid amino acid analogue protease inhibitor (carbobenzoxy-ala-ala-borophe; DK120) was described by Kinder, et al. ((1985) *J Med Chem* 28:1917; (1992) *Invasion Metastasis* 12:309).

Apoptotic protease is purified from cell lysates by affinity chromatography on the DK120 column. One ml of affinity resin is equilibrated with starting buffer (50 mM Tris pH 7.5, 100 mM NaCl, 1.0 mM CaCl$_2$, 0.1% NaN$_3$, and 0.05% Tween 20). Cell lysate is mixed with the resin and allowed to bind for 60 min. The column is then washed with starting buffer at 0.5 ml/min until the $OD_{280}$ returns to baseline. Bound material is eluted with starting buffer plus 0.1% HCl pH 4.5. During elution, 1.0 ml fractions are collected and immediately neutralized to pH 7.5. The column is regenerated by washing with 2.0 M NaCl (no additional protease is eluted during this step).

2. Screening Assay for Inhibitors of Proteolytic Activity

Assays are set up in 96 well plates in triplicate. Test wells contain 0.02 ml of affinity purified apoptotic protease, 0.02 ml of test sample (peptide library or DK120 as a positive inhibitor control) and 0.16 ml of N-methoxysuccinyl-ala-ala-pro-val p-nitroanilide (SEQ ID NO: 3) (MAAPV) substrate in PBS, pH 7.5. Assays are incubated at room temperature for 3–6 hr with periodic readings of OD at 405 nm. 1 U of enzyme activity is calculated as the amount of enzyme that hydrolyzes 1 nmol substrate/h.

If one or more of the peptides in the libraries serves as substrates for apoptotic proteases, test samples can be preincubated with apoptotic protease for 30 min prior to addition of the chromogenic substrate. This allows time for endogenous peptide substrates to be largely degraded, as reported previously for the identification of trypsin inhibitors from peptide libraries (Eichler et al. (1993) Biochem 32:11035–11041).

3. DNA Fragmentation in Isolated Nuclei

Libraries are also tested for inhibition of apoptotic protease-induced DNA fragmentation in isolated U937 nuclei. Like the protease assay, this procedure is simple, rapid and can be completed in one day. The natural substrate of apoptotic protease is currently not known. Thus, some samples that are positive in the protease assay with chromogenic substrate may not be active in the nuclear assay. However, the identification of inhibitors in the nuclear assay is more biologically relevant than the synthetic substrate assay.

Briefly, U937 cells are labeled with $^3$H-thymidine by culturing overnight with isotope at 0.5 mCi/ml. The cells are pelleted, washed once, and the cytoplasmic membrane lysed by resuspending the cells in assay buffer (50 mM Tris, 250 mM sucrose 10 mM $MgSO_4$, pH 7.5) plus 0.02% NP-40. Nuclei are then pelleted and resuspended in assay buffer at $1 \times 10^6$/ml. The assay is set up in triplicate in flat bottom microtiter plates under sterile conditions. Nuclei (0.05 ml) are mixed with 0.05 ml of sample diluted in 50 mM Tris pH 7.5 or buffer alone to determine total counts. Plates are incubated for 5 h at 37° C., and then harvested by the addition of 0.1 ml of harvesting buffer (10 mM Tris, 10 mM EDTA, 0.3% Triton X-100, pH 7.5). High molecular weight DNA is collected by filtration onto glass fiber paper and the radioactivity counted on a Packard Matrix 96 beta counter. Percent DNA fragmentation is calculated relative to the total high MW DNA recovered from control cells. The spontaneous release of $^3$H-thymidine relative to the total counts at the initiation of the assay does not exceed 2%/h for up to 7 h.

4. TNF and anti-Fas-induced Apoptosis of U937 Cells

Samples positive in the nuclear assay are tested for inhibition of apoptosis in whole U937 cells as measured by release of $^3$H-thymidine-labeled DNA fragments in microtiter plates. This assay eliminates potential drug candidates that are highly toxic or unable to penetrate cell membranes.

Samples are first tested for inhibition of TNF-induced apoptosis in a 3 h assay. The specificity of positive samples is then evaluated by testing their effects on anti-Fas-induced apoptosis of U937 cells. For example, a drug candidate for liver damage due to sepsis is preferably selective for the TNF-activated apoptotic pathway while leaving anti-Fas responses intact. However, compounds that block anti-Fas responses may also be clinically useful for other conditions.

The DNA fragmentation assay using whole cells was described in detail previously (Wright et al. (1992) *J Cell Biochem* 48:344–355), and the results correlate with the release of internucleosomal DNA fragments as detected by agarose gel electrophoresis. The assay is set up the same as for the isolated nuclei assay, except the cells are not lysed, and the assay is incubated 2–3 h. Drug candidates or the DK120 positive inhibitor control for TNF (but not for anti-Fas) are preincubated with the cells 30 mim prior to addition of TNF. Wells containing the drug candidates are examined microscopically just prior to harvesting the assay to detect any toxic effects. If compounds are toxic by causing necrosis, the DNA will not fragment, and thus will give the appearance of a false positive inhibitor. However, any necrotic effects are easily be detected by microscopic examination. Potential drugs are also be tested without TNF or anti-Fas to determine if they alone induce apoptosis. This assay eliminates drug candidates with overt toxicity in short term cultures.

A given library may contain one or more highly toxic species that masks the inhibition of TNF-induced apoptosis by a different species. Thus, if a given library potently inhibits both proteolytic activity against the synthetic substrate as well as induction of DNA fragmentation in isolated nuclei, deconvolution is performed using the synthetic substrate and isolated nuclei assays to identify the most active amino acid residues. At each step of the deconvolution, the contaminating toxic species becomes progressively more diluted with a concomitant increase in the concentration of the inhibitor. Thus, the enriched library loses toxicity in the whole cell assay.

5. TNF-induced Apoptosis of Isolated Murine Hepatocytes

Drug candidates that are effective inhibitors of TNF-induced apoptosis of U937 cells can then be tested for their effects on TNF-induced apoptosis of murine hepatocytes in vitro. The best drug candidates are typically not tested until they have been deconvoluted down to at least the $X_2$ position. The ability to suppress TNF-included apoptosis in hepatocytes is the most clinically relevant of these in vitro assays.

Briefly, murine hepatocytes will be isolated by the collagenase perfusion method disclosed by Leist et al. to demonstrate TNF-induced apoptosis of primary cultured murine hepatocytes (Leist et al. (1994) *J Immunol* 153:1778–1786). Cells are plated at $2 \times 10^4$ cells/well in RPMI 1604+10% FCS in 96 well microtiter plates. They are allowed to adhere for 5 h, and then the medium is replaced with RPMI 1640 without serum. Target cells are pretreated with Actinomycin D, 0.33 mM for 30 min prior to the addition of TNF 10 ng/ml. Drug candidates as well as the DK120 as a positive inhibitor control will also be incubated with the cells for 30 min prior to the addition of TNF. The assay is then incubated for 20 h, and cell viability assessed by the ability to produce formazan from MTT according to the method of Mossman ((1983) *J Immunol Methods* 65:55). Drug candidates will also be tested alone to detect any toxic effects.

Alternatives to this approach include the use of rats as a bigger source of hepatocytes, and the use the HepG2 human hepatoma cell line. This cell line grows rapidly in culture and has been shown by Leist et al. ((1994) *J Immunol* 153:1778–1786), to undergo TNF-induced apoptosis in the presence of Actinomycin D.

6. Toxicity Studies on Best Drug Candidates

The most promising drug candidates based on the screening assays are further evaluated for toxicity in vitro and in vivo. The above screening assays will eliminate compounds that are toxic to U937 or hepatozytes, at least in short term culture. Further studies are conducted to evaluate potential toxicity to normal endothelial cells and fibroblasts in 3 day proliferation assays. Different concentrations of compounds are added to normal human umbilical venous endothelial cells and fibroblasts in microtiter plates. After 48 h of culture, cells are pulsed with $^3$H-thymidine and the assay terminated after an additional 24 h culture. Cell viability is assessed by incorporation of isotope.

Compounds that are nontoxic in vitro are tested for acute toxicity in mice. Groups of 4 mice each are injected with compounds at doses ranging from 1.0 to 100 mg/kg. and observed for any lethal effects for at least 1 wk. These studies are designed to eliminate highly toxic compounds and establish approximate dosages for testing in the initial animal models as describes below. The best drug candidate will undergo more thorough toxicity testing in Phase II studies.

7. Test Best Drug Candidates in Murine Model of TNF-induced Hepatotoxicity

This model is performed as described by Leist et al. ((1994) *J Immunol* 153:1778–1786.; (1995) *J Immunol* 154:1307–1316). Briefly, mice are injected with drug candidates as well as DK120 as a positive control followed by TNF and Actinomycin D. After 12 h, serum samples are obtained from some of the mice for transaminase assays. The rest of the mice are observed for mortality for up to 1 wk.

The foregoing description of the preferred embodiments of the invention has been presented for purposes of illustration and description. They are not intended to be exhaustive or to limit the invention to the precise form disclosed, and many modifications and variations are possible in light of the above teaching.

The references discussed herein are provided solely for their disclosure prior to the filing date of the present application. Nothing herein is to be construed that the inventors are not entitled to antedate such disclosure by virtue of prior invention.

All publications, patents, and patent applications herein are incorporated by reference to the same extent as if each individual publication, patent, or patent application was specifically and individually indicated to be incorporated by reference.

Such modifications and variations which may be apparent to a person skilled in the art are intended to be within the scope of this invention.

---

What is claimed is:

1. A method for identifying an inhibitor of a mammalian protease of 24 kDa having the amino acid composition as follows expressed in number of residues per molecule: 25 asx; 7 thr; 15 ser; 30 glx; 6 pro; 43 gly; 17 ala; 16 val; 3 met; 10 ile; 22 leu; 39 nleu; 5 tyr; 8 phe; 7 his; 8 lys; 13 arg; with trp not determined, comprising screening a candidate inhibitor for an ability to inhibit proteolytic activity of said protease on a substrate.

2. The method of claim 1, wherein said substrate is synthetic.

* * * * *